(12) United States Patent
Nirogi et al.

(10) Patent No.: US 8,003,670 B2
(45) Date of Patent: Aug. 23, 2011

(54) AMINOALKOXY ARYL SULFONAMIDE COMPOUNDS AND THEIR USE AS 5-HT$_6$ LIGANDS

(75) Inventors: Ramakrishna Nirogi, Hyderabad (IN); Rama Sastri Kambhampati, Hyderabad (IN); Anil Karbhari Shinde, Hyderabad (IN); Anand Vijaykumar Daulatabad, Hyderabad (IN); Adi Reddy Dwarampudi, Hyderabad (IN); Nagaraj Vishwottam Kandikere, Hyderabad (IN); Santosh Vishwakarma, Hyderabad (IN); Venkateswarlu Jasti, Hyderabad (IN)

(73) Assignee: Suven Life Sciences Limited, Hydersbad (IN)

( * ) Notice: Subject to any disclaimer, the term of this patent is extended or adjusted under 35 U.S.C. 154(b) by 0 days.

(21) Appl. No.: 12/598,616

(22) PCT Filed: Apr. 15, 2008

(86) PCT No.: PCT/IN2008/000247
§ 371 (c)(1),
(2), (4) Date: Nov. 3, 2009

(87) PCT Pub. No.: WO2008/136017
PCT Pub. Date: Nov. 13, 2008

(65) Prior Publication Data
US 2010/0087484 A1      Apr. 8, 2010

(30) Foreign Application Priority Data
May 3, 2007   (IN) .............................. 940/CHE/2007

(51) Int. Cl.
*A61K 31/454*   (2006.01)
*A61K 31/405*   (2006.01)
*C07D 401/12*   (2006.01)
*C07D 209/04*   (2006.01)

(52) U.S. Cl. ........ 514/323; 514/415; 546/201; 548/469; 548/511

(58) Field of Classification Search .................. 514/323, 514/415; 546/201; 548/469, 511
See application file for complete search history.

(56) References Cited

FOREIGN PATENT DOCUMENTS

| WO | WO 98/27081 | 6/1998 |
|---|---|---|
| WO | WO 99/02502 | 1/1999 |
| WO | WO 99/37623 | 7/1999 |
| WO | WO 99/42465 | 8/1999 |
| WO | WO 00/63203 | 10/2000 |
| WO | WO 01/32646 | 5/2001 |
| WO | WO 02/36562 | 5/2002 |
| WO | WO 02/060871 | 8/2002 |
| WO | WO 02/098857 | 12/2002 |
| WO | WO 02/098878 | 12/2002 |
| WO | WO 03/013510 | 2/2003 |
| WO | WO 03/065046 | 8/2003 |
| WO | WO 03/066056 | 8/2003 |
| WO | WO 03/080580 | 10/2003 |
| WO | WO 2004/048328 | 6/2004 |
| WO | WO 2004/048330 | 6/2004 |
| WO | WO 2004/048331 | 6/2004 |
| WO | WO 2004/055026 | 7/2004 |
| WO | WO 2004056361 A1 * | 7/2004 |
| WO | WO 2005/013974 | 2/2005 |
| WO | WO 2006038594 A1 * | 4/2006 |
| WO | WO 2007/020652 | 2/2007 |

OTHER PUBLICATIONS

Vippagunta et al., Advanced Drug Delivery Reviews, vol. 48, p. 3-26 (on p. 3), 2001.*

(Continued)

*Primary Examiner* — Yong Chu
(74) *Attorney, Agent, or Firm* — IP Horgan Ltd.

(57) ABSTRACT

The present invention relates to novel aminoalkoxy arylsulfonamide compounds of the formula (I), their derivatives, their stereoisomers, their pharmaceutically acceptable salts and pharmaceutically acceptable compositions containing them. The present invention also relates to a process for the preparation of above said novel compounds, their derivatives, their stereoisomers, their pharmaceutically acceptable salts and pharmaceutically acceptable compositions containing them. These compounds are useful in the treatment of various disorders that are related to 5-HT$_6$ receptor functions. Specifically, the compounds of this invention are also useful in the treatment of various CNS disorders, hematological disorders, eating disorders, diseases associated with pain, respiratory diseases, genito-urological disorders, cardiovascular diseases and cancer.

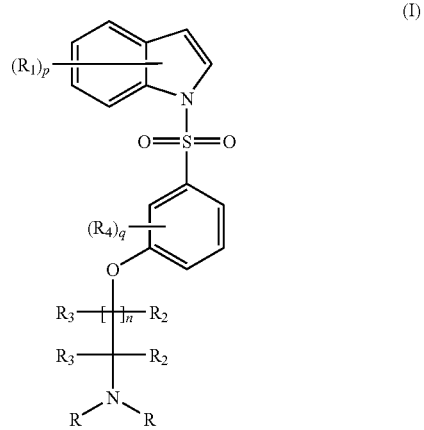

(I)

8 Claims, No Drawings

OTHER PUBLICATIONS

Monsma et al., Molec. Pharmacol. 43:320-327 (1993).
Kohen et al., J. Neurochem. 66:47-56 (1996).
Ruat et al., Biochem. Biophys. Res. Comm. 193:268-276 (1993).
Ward et al., Neurosci. 64:1105-1111 (1995).
Reavill and Rogers, Curr. Opin. Invest. Drugs 2(1):104-109 (2001).
Stean et al., Br. J. Pharmacol. 127 Proc. Supplement 131P (1999).
Routledge et al., Br. J. Pharmacol. 130:1606-1612 (2000).
Gerard et al., Brain Research 746:207-219 (1997).
Bentley et al., Br. J. Pharmacol. 126(7):1537-1542 (1999).
Dawson et al., Br. J. Pharmacol. 130(1):23-26 (2000).
Rogers et al., Society of Neuroscience, Abstracts 26:680 (2000).
Ernst et al., J. Neuroscience 18(15):5901-5907 (1998).
Cole et al., WAY-181187 230th ACS National Meet. (Aug. 28-Sep. 1, 2005 Wash.D.C.) Abstract MEDI 17.
Branchek and Blackburn, Ann. Rev. Pharm. Toxicol. 40:319-334 (2000).
Roth et al., J. Pharmacol. Exper. Therapeut. 268:1403-12 (1994).
Fox et al., J. Neurochem. 65(6):2796-99 (1995).
Wooley et al., Neuropharmacol. 41:210-29 (2001).
Holenz et al., Drug Discovery Today 11(7/8):283-299 (Apr. 2006).
Glennon et al., J. Med. Chem. 43:1011-1018 (2000).
Tsai et al., Bioorg. Med. Chem. Lett. 10:2295-99 (2000).
Demchyshyn et al., 31st Ann. Meet. Soc. Neurosci. Nov. 10-15, Abstr. 266.6 (2001).
Mattson et al., Bioorg. Med. Chem. Lett. 15:4230-34 (2005).
Pullagurla MR, Westkaemper RB, Glennon RA, "Possible differences in modes of agonist and antagonist binding at human 5-HT6 receptors." Bioorg. Med. Chem. Lett. 14:4569-4573 (2004).
Bromidge et al., J. Med. Chem. 42:202-205 (1999).
Bromidge et al., Bioorg. Med. Chem. Lett. 11:55-58 (2001).
Hirst et al., 33rd Ann. Meet. Soc. Neurosci. (Nov. 8-12 New Orleans) Abstr. 576.7 (2003).
Bonhaus et al., 32nd Ann. Meet. Soc. Neurosci. Abstr. 884.5 (2002).
Sleight et al., Br. J. Pharmacol. 124:556-62 (1998).
Pouzet et al., Pharmacol. Biochem. Behav. 71:635-643 (2002).
Berge et al., J. Pharm. Sci. 66:1-19 (1977).
Kask et al., Eur. J. PHarmacol. 414:215-224 (2001).
Turnbull et al., Diabetes 51:2441-2449 (2002).
Ennaceur, Behav. Brain Res. 31:47-59 (1988).
King et al., Neuropharmacol. 47:195-204 (2004).
Yamada et al., Pharmacol. Biochem. and Behaviour 78:787-91 (2004).
Lindner et al., J. Pharmacol. Exp. Therap. 307(2):682-91 (2003).
International Search Report issued in counterpart PCT Appln. No. PCT/IN2008/000247, (2008).
Written Opinion issued in counterpart PCT Appln. No. PCT/IN2008/000247, (2009).
International Preliminary Report on Patentability issued in counterpart PCT Appln. No. PCT/IN2008/000247, (2009).

* cited by examiner

AMINOALKOXY ARYL SULFONAMIDE COMPOUNDS AND THEIR USE AS 5-$HT_6$ LIGANDS

CROSS-REFERENCE TO RELATED APPLICATIONS

This is a Sect. 371 National Stage of PCT International Application No. PCT/IN2008/000247, filed on Apr. 15, 2008, claiming priority of Indian Patent Application No. 940/CHE/2007 filed on May 3, 2007, the contents of both applications hereby being incorporated by reference.

FIELD OF INVENTION

The present invention relates to novel aminoalkoxy arylsulfonamide compounds of the formula (I), their derivatives, their stereoisomers, their pharmaceutically acceptable salts and pharmaceutically acceptable compositions containing them.

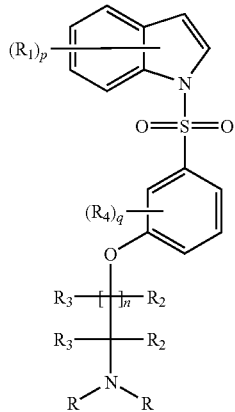

The present invention also relates to a process for the preparation of above said novel compounds, their derivatives, their stereoisomers, their pharmaceutically acceptable salts and pharmaceutically acceptable compositions containing them.

These compounds are useful in the treatment of various disorders that are related to 5-$HT_6$ receptor functions. Specifically, the compounds of this invention are also useful in the treatment of various CNS disorders, hematological disorders, eating disorders, diseases associated with pain, respiratory diseases, genito-urological disorders, cardiovascular diseases and cancer.

BACKGROUND OF THE INVENTION

Various central nervous system disorders such as anxiety, depression, motor disorders etc., are believed to involve a disturbance of the neurotransmitter 5-hydroxytryptamine or serotonin. Serotonin is localized in the central and peripheral nervous systems and is known to affect many types of conditions including psychiatric disorders, motor activity, feeding behavior, sexual activity and neuroendocrine regulation among others. 5-HT receptor subtypes regulate the various effects of serotonin. Known 5-HT receptor family includes the 5-$HT_1$ family (e.g. 5-$HT_{1A}$), the 5-$HT_2$ family (e.g. 5-$HT_{2A}$), 5-$HT_3$, 5-$HT_4$, 5-$HT_5$, 5-$HT_6$ and 5-$HT_7$ subtypes.

The 5-$HT_6$ receptor subtype was first cloned from rat tissue in 1993 (Monsma, F. J.; Shen, Y.; Ward, R. P.; Hamblin, M. W., Sibley, D. R., Molecular Pharmacology, 1993, 43, 320-327) and subsequently, from human tissue (Kohen, R.; Metcalf, M. A.; Khan, N.; Druck, T.; Huebner, K.; Sibley, D. R., Journal of Neurochemistry, 1996, 66, 47-56). The receptor is a G-protein coupled receptor (GPCR) positively coupled to adenylate cyclase (Ruat, M.; Traiffort, E.; Arrang, J-M.; Tardivel-Lacombe, L.; Diaz, L.; Leurs, R.; Schwartz, J-C., Biochemical Biophysical Research Communications, 1993, 193, 268-276). The receptor is found almost exclusively in the central nervous system (CNS) areas both in rats as well as in humans.

In situ hybridization studies of 5-$HT_6$ receptor in rat brain using mRNA indicate principal localization in the areas of 5-HT projection including striatum, nucleus accumbens, olfactory tubercle and hippocampal formation (Ward, R. P.; Hamblin, M. W.; Lachowicz, J. E.; Hoffman, B. J.; Sibley, D. R.; Dorsa, D. M., Neuroscience, 1995, 64, 1105-1111). Highest levels of 5-$HT_6$ receptor mRNA has been observed in the olfactory tubercle, the striatum, nucleus accumbens, dentate gyrus as well as $CA_1$, $CA_2$ and $CA_3$ regions of the hippocampus. Lower levels of 5-$HT_6$ receptor mRNA were seen in the granular layer of the cerebellum, several diencephalic nuclei, amygdala and in the cortex. Northern blots have revealed that 5-$HT_6$ receptor mRNA appears to be exclusively present in the brain, with little evidence for its presence in peripheral tissues.

The high affinity of number of antipsychotic agents towards 5-$HT_6$ receptor, the localization of its mRNA in striatum, olfactory tubercle and nucleus accumbens suggests that some of the clinical actions of these compounds may be mediated through this receptor. Its ability to bind a wide range of therapeutic compounds used in psychiatry, coupled with its intriguing distribution in the brain has stimulated significant interest in new compounds which are capable of interacting with the said receptor (Ref: Sleight, A. J. et al. (1997) 5-$HT_6$ and 5-$HT_7$ receptors: molecular biology, functional correlates and possible therapeutic indications, Drug News Perspect. 10, 214-224). Significant efforts are being made to understand the possible role of the 5-$HT_6$ receptor in psychiatry, cognitive dysfunction, motor function and control, memory, mood and the like. The compounds which demonstrate a binding affinity for the 5-$HT_6$ receptor are earnestly sought both as an aid in the study of the 5-$HT_6$ receptor and as potential therapeutic agents in the treatment of central nervous system disorders, for example see Reavill C. and Rogers D. C., Current Opinion in Investigational Drugs, 2001, 2(1): 104-109, Pharma Press Ltd.

Monsma F. J. et al. (1993) and Kohen, R. et al. (2001) have shown that several tricyclic antidepressant compounds, such as amitriptyline and atypical antidepressant compounds, such as mianserin have high affinity for the 5-$HT_6$ receptor. These findings have led to the hypothesis that the 5-$HT_6$ receptor is involved in the pathogenesis and/or treatment of affective disorders. Rodent models of anxiety-related behavior yield conflicting results about the role of the 5-$HT_6$ receptor in anxiety. Treatment with 5-$HT_6$ receptor antagonists increases seizure threshold in a rat maximal electroconvulsive-shock test [Stean, T. et al. (1999) Anticonvulsant properties of the selective 5-$HT_6$ receptor antagonist SB-271046 in the rat maximal electroshock seizure threshold test. Br. J. Pharmacol. 127, 131P; Routledge, C. et al. (2000) Characterization of SB-271046: a potent, selective and orally active 5-$HT_6$) receptor antagonist. Br. J. Pharmacol. 130, 1606-1612].

Although this indicates that 5-HT$_6$ receptors might regulate seizure threshold, the effect is not as pronounced as that of known anticonvulsant drugs.

Our understanding of the roles of 5-HT$_6$ receptor ligands is most advanced in two therapeutic indications in which this receptor is likely to have a major role: learning and memory deficits and abnormal feeding behaviour. The exact role of the 5-HT$_6$ receptor is yet to be established in other CNS indications such as anxiety; although one 5-HT$_6$ agonist has reached Phase I clinical trials recently, the exact role of the receptor is still to be established and is the focus of significant investigation. There are many potential therapeutic uses for 5-HT$_6$ receptor ligands in humans based on direct effects and on indications from available scientific studies. These studies include the localization of the receptor; the affinity of ligands with known in-vivo activity and various animal studies conducted so far. Preferably, antagonist compounds of 5-HT$_6$ receptors are sought after as therapeutic agents.

One potential therapeutic use of modulators of 5-HT$_6$ receptor functions is in the enhancement of cognition and memory in human diseases such as Alzheimer's. The high levels of receptor found in structures such as the forebrain, including the caudate/putamen, hippocampus, nucleus accumbens and cortex suggests a role for the receptor in memory and cognition since these areas are known to play a vital role in memory (Gerard, C.; Martres, M. P.; Lefevre, K.; Miguel, M. C.; Verge, D.; Lanfumey, R.; Doucet, E.; Hamon, M.; EI Mestikawy, S., Brain Research, 1997, 746, 207-219). The ability of known 5-HT$_6$ receptor ligands to enhance cholinergic transmission also supports the potential cognition use (Bentey, J. C.; Boursson, A.; Boess, F. G.; Kone, F. C.; Marsden, C. A.; Petit, N.; Sleight, A. J., British Journal of Pharmacology, 1999, 126 (7), 1537-1542).

Studies have found that a known 5-HT$_6$ selective antagonist significantly increased glutamate and aspartate levels in the frontal cortex without elevating levels of noradrenaline, dopamine or 5-HT. This selective elevation of certain neurochemicals is noted during memory and cognition, strongly suggests a role for 5-HT$_6$ ligands in cognition (Dawson, L. A.; Nguyen, H. Q.; Li, P. British Journal of Pharmacology, 2000, 130 (1), 23-26). Animal studies of memory and learning with a known selective 5-HT$_6$ antagonist has some positive effects (Rogers, D. C.; Hatcher, P. D.; Hagan, J. J. Society of Neuroscience, Abstracts, 2000, 26, 680).

A related potential therapeutic use for 5-HT$_6$ ligands is in the treatment of attention deficit disorders (ADD, also known as Attention Deficit Hyperactivity Disorder or ADHD) in children as well as adults. As 5-HT$_6$ antagonists appear to enhance the activity of the nigrostriatal dopamine pathway and AMID has been linked to abnormalities in the caudate (Ernst, M; Zametkin, A. J.; Matochik, J. H.; Jons, P. A.; Cohen, R. M., Journal of Neuroscience, 1998, 18(15), 5901-5907), 5-HT$_6$ antagonists may attenuate attention deficit disorders.

At present, a few fully selective agonists are available. The Wyeth agonist WAY-181187 is currently in Phase I trials to target anxiety [Cole, D. C. et al. (2005) Discovery of a potent, selective and orally active 5-HT$_6$ receptor agonist, WAY-181187. 230th ACS Natl. Meet. (August 28-September 1, Washington D. C.), Abstract MEDI 17.]

International Patent Publication WO 03/066056 A1 reports that antagonism of 5-HT$_6$ receptor could promote neuronal growth within the central nervous system of a mammal. Another International Patent Publication WO 03/065046 A2 discloses new variant of human 5-HT$_6$ receptor and proposes that 5-HT$_6$ receptor is associated with numerous other disorders.

Early studies examining the affinity of various CNS ligands with known therapeutic utility or a strong structural resemblance to known drugs suggests a role for 5-HT$_6$ ligands in the treatment of schizophrenia and depression. For example, clozapine (an effective clinical antipsychotic) has high affinity for the 5-HT$_6$ receptor subtype. Also, several clinical antidepressants have high affinity for the receptor as well and act as antagonists at this site (Branchek, T. A.; Blackburn, T. P., Annual Reviews in Pharmacology and Toxicology, 2000, 40, 319-334).

Further, recent in-vivo studies in rats indicate that 5-HT$_6$ modulators may be useful in the treatment of movement disorders including epilepsy (Stean, T.; Routledge, C.; Upton, N., British Journal of Pharmacology, 1999, 127 Proc. Supplement-131P; and Routledge, C.; Bromidge, S. M.; Moss, S. F.; Price, G. W.; Hirst, W.; Newman, H.; Riley, G.; Gager, T.; Stean, T.; Upton, N.; Clarke, S. E.; Brown, A. M., British Journal of Pharmacology, 2000, 30 (7), 1606-1612).

Taken together, the above studies strongly suggest that compounds which are 5-HT$_6$ receptor modulators, i.e. ligands, may be useful for therapeutic indications including, the treatment of diseases associated with a deficit in memory, cognition and learning such as Alzheimer's and attention deficit disorder; the treatment of personality disorders such as schizophrenia; the treatment of behavioral disorders, e.g. anxiety, depression and obsessive compulsive disorders; the treatment of motion or motor disorders such as Parkinson's disease and epilepsy; the treatment of diseases associated with neurodegeneration such as stroke or head trauma; or withdrawal from drug addiction including addiction to nicotine, alcohol and other substances of abuse.

Such compounds are also expected to be of use in the treatment of certain gastrointestinal (GI) disorders such as functional bowel disorder. See for example, Roth, B. L.; et al., Journal of Pharmacology and Experimental Therapeutics, 1994, 268, pages 1403-1412; Sibley, D. R.; et al., Molecular Pharmacology, 1993, 43, 320-327, Sleight, A. J.; et al., Neurotransmission, 1995, 11, 1-5; and Sleight, A. J.; et al., Serotonin ID Research Alert, 1997, 2(3), 115-118.

Furthermore, the effect of 5-HT$_6$ antagonist and 5-HT$_6$ antisense oligonucleotides to reduce food intake in rats has been reported, thus potentially in treatment of obesity. See for example, Bentey, J. C.; Boursson, A.; Boess, F. G.; Kone, F. C.; Marsden, C. A.; Petit, N.; Sleight, A. J., British Journal of Pharmacology, 1999, 126 (7), 1537-1542); Wooley et al., Neuropharmacology, 2001, 41: 210-129; and WO 02/098878.

Recently a review by Holenz, Jo"rg et. al., Drug Discovery Today, 11, 7/8, Apr. 2006, Medicinal chemistry strategies to 5-H$_6$ receptor ligands as potential cognitive enhancers and antiobesity agents, gives elaborate discussion on evolution of 5-HT$_6$ ligands. It had summarized pharmacological tools and preclinical candidates used in evaluation of 5-HT$_6$ receptor in illnesses such as schizophrenia, other dopamine-related disorders and depression and to profile the neurochemical and electrophysiological effects of either blockade or activation of 5-HT$_6$ receptors. Furthermore, they have been used to characterize the 5-HT$_6$ receptor and to investigate its distribution.

So far several clinical candidates form the part of indole-type structures and are closely related structurally to the endogenous ligand 5-HT, for example compounds by Glennon, R. A. et. al., 2-Substituted tryptamines: agents with selectivity for 5-HT$_6$ serotonin receptors, J. Med. Chem. 43, 1011-1018, 2000; Tsai, Y. et. al., N1-(Benzenesulfonyl) tryptamines as novel 5-HT$_6$ antagonists, Bioorg. Med. Chem. Lett. 10, 2295-2299, 2000; Demchyshyn L. et al., ALX-1161:

pharmacological properties of a potent and selective 5-HT$_6$ receptor antagonist, 31st Annu. Meet. Soc. Neurosci. (November 10-15), Abstract 266.6, 2001; Slassi, A. et. al., Preparation of 1-(arylsulfonyl)-3-(tetrahydropyridinyl)indoles as 5-HT$_6$ receptor inhibitors, WO 200063203, 2000; Mattsson, C. et. al., Novel, potent and selective 2-alkyl-3-(1,2,3,6-tetrahydropyridin-4-yl)-1H-indole as 5-HT$_6$ receptor agonists, XVIIth International Symposium on Medicinal Chemistry, 2002; Mattsson, C. et. al., 2-Alkyl-3-(1,2,3,6-tetrahydropyridin-4-yl)-1H-indoles as novel 5-HT$_6$ receptor agonists, Bioorg. Med. Chem. Lett. 15, 4230-4234, 2005]

Structure functionality relationships are described in the section on indole-like structures (and in a receptor-modeling study in which Pullagurla et. al., claim different binding sites for agonists and antagonists [Pullagurla, M. R. et al. (2004) Possible differences in modes of agonist and antagonist binding at human 5-HT$_6$ receptors. Bioorg. Med. Chem. Lett. 14, 4569-4573]. Most antagonists that are reported form part of the monocyclic, bicyclic and tricyclic aryl-piperazine classes [Bromidge, S. M. et. al., (1999) 5-Chloro-N-(4-methoxy-3-piperazin-1-ylphenyl)-3-methyl-2-benzothiophenesulfonamide (SB-271046): A potent, selective and orally bioavailable 5-HT$_6$ receptor antagonist. J. Med. Chem. 42, 202-205; Bromidge, S. M. et al. (2001) Phenyl benzenesulfonamides are novel and selective 5-HT$_6$ antagonists: Identification of N-(2,5-dibromo-3-fluorophenyl)-4-methoxy-3-piperazin-1-ylbenzenesulfonamide (SB-357134). Bioorg. Med. Chem. Lett. 11, 55-58; Hirst, W. D. et al. (2003) Characterisation of SB-399885, a potent and selective 5-HT$_6$ receptor antagonist. 33$^{rd}$ Annu. Meet. Soc. Neurosci. (Nov. 8-12, New Orleans), Abstract 576.7; Stadler, H. et al. (1999) 5-HT$_6$ antagonists: A novel approach for the symptomatic treatment of Alzheimer's disease. 37$^{th}$ IUPAC Cong. Berlin, Abstract MM-7; Bonhaus, D. W. et al. (2002) Ro-4368554, a high affinity, selective, CNS penetrating 5-HT$_6$ receptor antagonist. 32$^{nd}$ Annu. Meet. Soc. Neurosci., Abstract 884.5.; Beard, C. C. et al. (2002) Preparation of new indole derivatives with 5-HT$_6$ receptor affinity. WO patent 2002098857).

Ro 63-0563: Potent and selective antagonists at human and rat 5-HT$_6$ receptors. Br. J. Pharmacol. 124, (556-562). Phase II antagonist candidate from GlaxoSmithKline, SB-742457 for the therapeutic indication of cognitive dysfunction associated with Alzheimer's disease [Ahmed, M. et al. (2003) Novel compounds. WO patent 2003080580], and the Lilly compound LY-483518 [Filla, S. A. et al. (2002) Preparation of benzenesulfonic acid indol-5-yl esters as antagonists of the 5-HT$_6$ receptor. WO 2002060871]. SB-271046, the first 5-HT$_6$ receptor antagonist to enter Phase I clinical development, has been discontinued (probably because of low penetration of the blood-brain barrier). In addition, the selective 5-HT$_6$ receptor antagonist SB-271046 is inactive in animal tests related to either positive or negative symptoms of schizophrenia [Pouzet, B. et al. (2002) Effects of the 5-HT$_6$ receptor antagonist, SB-271046, in animal models for schizophrenia. Pharmacol. Biochem. Behay. 71, 635-643].

International Patent Publications WO 2004/055026 A1, WO 2004/048331 A1, WO 2004/048330 A1 and WO 2004/048328 A2 (all assigned to Suven Life Sciences Limited) describe the related prior art. Further WO 98/27081, WO 99/02502, WO 99/37623, WO 99/42465 and WO 01/32646 (all assigned to Glaxo SmithKline Beecham PLC) disclose a series of aryl sulphonamide and sulphoxide compounds as 5-HT$_6$ receptor antagonists and are claimed to be useful in the treatment of various CNS disorders. While some 5-HT$_6$ modulators have been disclosed, there continues to be a need for compounds that are useful for modulating 5-HT$_6$. Surprisingly, it has been found that aminoalkoxy arylsulphonamide compounds of formula (I) demonstrate very high 5-HT$_6$ receptor affinity. Therefore, it is an object of this invention to provide compounds, which are useful as therapeutic agents in the treatment of a variety of central nervous system disorders or disorders affected by the 5-HT$_6$ receptor.

SUMMARY OF THE INVENTION

The present invention relates to novel aminoalkoxy azylsulfonamide compounds, of the formula (I), their derivatives, their stereoisomers, their pharmaceutically acceptable salts and pharmaceutically acceptable compositions containing them

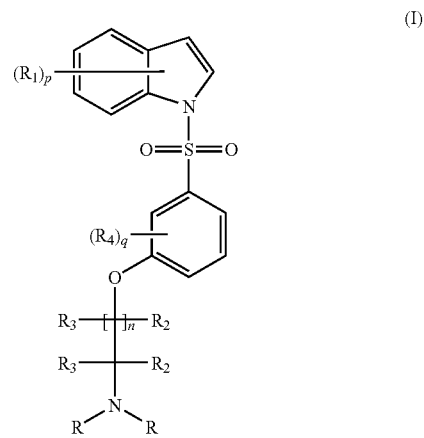

wherein $R_1$ represents hydrogen, hydroxyl, halogen, ($C_1$-$C_3$)alkyl thio, ($C_1$-$C_3$)alkyl, halo($C_1$-$C_3$)alkyl, ($C_1$-$C_3$) alkoxy, halo($C_1$-$C_3$)alkoxy, cyclo($C_3$-$C_6$)alkyl, cyclo($C_3$-$C_6$) alkoxy or cyclo alkyl($C_3$-$C_6$) alkoxy;

R, $R_2$, $R_3$ and $R_4$ may be same or different and each independently represent hydrogen, halogen, ($C_1$-$C_3$)alkyl, halo ($C_1$-$C_3$)alkyl, ($C_1$-$C_3$)alkoxy, halo($C_1$-$C_3$)alkoxy or cyclo alkyl($C_3$-$C_6$) alkoxy;

"n" represents 0 to 4;

"p" represents 0 to 6;

"q" represents 0 to 4;

Optionally R along with either $R_2$ or $R_3$ and the nitrogen atom may form heterocyclyl, which may be optionally substituted by one or more substituents selected from hydrogen, halogen, ($C_1$-$C_3$) alkyl, halo($C_1$-$C_3$)alkyl, ($C_1$-$C_3$)alkoxy or halo($C_1$-$C_3$)alkoxy;

The present invention relates to use of a therapeutically effective amount of compound of formula (I), to manufacture a medicament, in the treatment or prevention of a disorder involving selective affinity for the 5-HT$_6$ receptor.

Specifically, the compounds of this invention are also useful in the treatment of various CNS disorders, hematological disorders, eating disorders, diseases associated with pain, respiratory diseases, genito-urological disorders, cardiovascular diseases and cancer.

In another aspect, the invention relates to pharmaceutical compositions containing a therapeutically effective amount of at least one compound of formula (I) or individual stereoisomers, racemic or non-racemic mixture of stereoisomers or pharmaceutically acceptable salts or solvates thereof, in admixture with at least one suitable carrier.

In another aspect, the invention relates to compositions comprising and methods for using compounds of Formula (I).

In still another aspect, the invention relates to the use of a therapeutically effective amount of compound of formula (I), to manufacture a medicament, in the treatment or prevention of a disorder involving selective affinity for the 5-HT$_6$ receptor.

In yet another aspect, the invention further relates to the process for preparing compounds of formula (I).

Following is the Partial List of the Compounds Belonging to General Formula (I):

1-[3'-(N,N-dimethylamino ethoxy)benzenesulfonyl]-1H-indole;
5-Fluoro-1-[3'-(N,N-dimethylamino ethoxy)benzenesulfonyl]-1H-indole;
5-Bromo-1-(3'-[N,N-dimethylamino ethoxy)benzenesulfonyl]-1H-indole;
5-Fluoro-1-[3'-(N,N-dimethylamino propoxy)benzenesulfonyl]-1H-indole;
5-Bromo-1-[3'-(N,N-dimethylamino propoxy)benzenesulfonyl]-1H-indole;
1-[3'-(N,N-Dimethylamino propoxy)benzenesulfonyl]-5-methoxy-1H-indole;
1-[3'-(1-Methylpiperidin-4-yl oxy)benzenesulfonyl]-1H-indole;
5-Fluoro-1-[3'-(1-methylpiperidin-4-yl oxy)benzenesulfonyl]-1H-indole;
5-Methoxy-1-[3'-(1-methylpiperidin-4-yl oxy)benzenesulfonyl]-1H-indole;
1-[4'-Methyl-3'-(N,N-dimethylamino ethoxy)benzenesulfonyl]-1H-indole;
5-Fluoro-1-[4'-methyl-3'-(N,N-dimethylamino ethoxy)benzenesulfonyl]-1H-indole;
5-Bromo-1-[4'-methyl-3'-(N,N-dimethylamino ethoxy)benzenesulfonyl]-1H-indole;
1-[4'-Methyl-3'-(N,N-dimethylamino ethoxy)benzenesulfonyl]-5-methoxy-1H-indole;
5-Ethoxy-1-[4'-methyl-3'-(N,N-dimethylamino ethoxy)benzenesulfonyl]-1H-indole;
6-Chloro-1-[4'-methyl-3'-(N,N-dimethylamino ethoxy)benzenesulfonyl]-1H-indole;
1-[4'-Methyl-3'-(N,N-dimethylamino propoxy)benzenesulfonyl]-1H-indole;
5-Fluoro-1-[4'-Methyl-3'-(N,N-dimethylamino propoxy)benzenesulfonyl]-1H-indole;
5-Bromo-1-[4'-Methyl-3'-(N,N-dimethylamino propoxy)benzenesulfonyl]-1H-indole;
1-[4'-Methyl-3'-(N,N-dimethylamino propoxy)benzenesulfonyl]-5-methoxy-1H-indole;
5-Ethoxy-1-[4'-methyl-3'-(N,N-dimethylamino propoxy)benzenesulfonyl]-1H-indole;
6-Chloro-1-[4'-methyl-3'-(N,N-dimethylamino propoxy)benzenesulfonyl]-1H-indole;
6-Chloro-1-[4'-methyl-3'-(1-methyl piperidin-4-yl oxy)benzenesulfonyl]-1H-indole;
1-[4'-Methyl-3'-(1-methyl piperidin-4-yl oxy)benzenesulfonyl]-1H-indole;
5-Fluoro-1-(4'-methyl-3'-(1-methyl piperidin-4-yl oxy)benzenesulfonyl)-1H-indole hydrochloride;
4-Chloro-1-[4'-methyl-3'-(1-methyl piperidin-4-yl oxy)benzenesulfonyl]-1H-indole;
1-[4'-Ethyl-3'-(N,N-dimethylamino ethoxy)benzenesulfonyl]-1H-indole;
5-Bromo-1-[4'-ethyl-3'-(N,N-dimethylamino ethoxy)benzenesulfonyl]-1H-indole;
1-[4'-Ethyl-3'-(N,N-dimethylamino ethoxy)benzenesulfonyl]-5-methoxy-1H-indole;
6-Chloro-1-[4'-Ethyl-3'-(N,N-dimethylamino ethoxy)benzenesulfonyl]-1H-indole;
1-[4'-Ethyl-3'-(N,N-dimethylamino ethoxy)benzenesulfonyl]-5-fluoro-1H-indole;
1-[4'-Ethyl-3'-(N,N-dimethylamino propoxy)benzenesulfonyl]-1H-indole;
5-Bromo-1-[4'-Ethyl-3'-(N,N-dimethylamino propoxy)benzenesulfonyl]-1H-indole;
1-[4'-Ethyl-3'-(N,N-dimethylamino propoxy)benzenesulfonyl]-6-chloro-1H-indole;
1-[4'-Ethyl-3'-(N,N-dimethylamino propoxy)benzenesulfonyl]-5-methoxy-1H-indole;
1-[4'-Ethyl-3'-(N,N-dimethylamino propoxy)benzenesulfonyl]-5-fluoro-1H-indole;
1-[4'-Isopropyl-3'-(N,N-dimethylamino ethoxy)benzenesulfonyl]-1H-indole;
1-[4'-Isopropyl-3'-(N,N-dimethylamino ethoxy)benzenesulfonyl]-5-methoxy-3-methyl-1H-indole;
1-[4'-Isopropyl-3'-(1-dimethylamino-2-propoxy)benzenesulfonyl]-1H-indole;
1-[4'-Isopropyl-3'-(2-dimethylamino-1-propoxy)benzenesulfonyl]-1,1-indole;
1-[4'-Isopropyl-3'-(N,N-dimethylamino ethoxy)benzenesulfonyl]-3-methyl-1H-indole;
1-[4'-Isopropyl-3'-(N,N-d methylamino propoxy)benzenesulfonyl]-3-methyl-1H-indole;
1-[4'-Isopropyl-3'-(N,N-d methylamino ethoxy)benzenesulfonyl]-5-methoxy-1H-indole;
1-[4'-Isopropyl-3'-(N,N-dimethylamino propoxy)benzenesulfonyl]-5-Methoxy-1H-indole;
1-[4'-Isopropyl-3'-(2-dimethylamino propoxy)benzenesulfonyl]-5-Methoxy-1H-1-indole;
1-[4'-Isopropyl-3'-(1-dimethylamino-2-propoxy)benzenesulfonyl]-5-methoxy-1H-indole;
1-[4'-Isopropyl-3'-(N,N-dimethylamino ethoxy)benzenesulfonyl]-5-fluoro-1H-indole;
1-[4'-Isopropyl-3'-(N,N-dimethylamino propoxy)benzenesulfonyl]-5-fluoro-1H-indole;
1-[4'-Isopropyl-3'-(2-dimethylamino propoxy)benzenesulfonyl]-5-fluoro-1H-indole;
1-[4'-Isopropyl-3'-(1-dimethylamino-2-propoxy)benzenesulfonyl]-5-fluoro-1H-indole;
1-[4'-Isopropyl-3'-(N,N-dimethylamino ethoxy)benzene sulfonyl]-5-fluoro-3-methyl-1H-indole;
1-[4'-Isopropyl-3'-(N,N-dimethylamino propoxy)benzenesulfonyl]-5-fluoro-3-methyl-1H-indole;
5-Methoxy-1-[4'-isopropyl-3'-(1-methyl piperidin-4-yl oxy)benzenesulfonyl]-1H-indole;
5-Fluoro-1-[4'-isopropyl-3'-(1-methyl piperidin-4-yl oxy)benzenesulfonyl]-1H-indole;
3-Methyl-1-[4'-methyl-3'-(1-methyl piperidin-4-yl oxy)benzenesulfonyl]-1H-indole;
5-Methoxy-1-[4-ethyl-3-(1-methyl piperidin-4-yl oxy)benzenesulfonyl]-1H-indole;
5-Methoxy-1-[4'-methoxy-3'-(piperidin-4-yl oxy)benzenesulfonyl]-1H-indole hydrochloride;
5-Methoxy-1-[4'-methoxy-3'-(1-methyl piperidin-4-yl oxy)benzenesulfonyl]-1H-indole;
5-Fluoro-1-[4'-methoxy-3'-(1-methyl piperidin-4-yl oxy)benzenesulfonyl]-1H-indole;
5-Fluoro-1-[4'-chloro-3'-(1-methyl piperidin-4-yl oxy)benzenesulfonyl]-1H-indole;
5-Fluoro-3-methyl-1-[4'-methoxy-3'-(1-methyl piperidin-4-yl oxy)benzenesulfonyl]-1H-indole;
5-Methoxy-3-methyl-1-[4'-isopropyl-3'-(1-methyl piperidin-4-yl oxy)benzenesulfonyl]-1H-indole;
6-Chloro-1-[4-methoxy-3'-(1-methyl piperidin-4-yl oxy)benzenesulfonyl]-1H-indole;

5-Bromo-1-[4'-methoxy-3'-(1-methyl piperidin-4-yl oxy) benzenesulfonyl]-1H-indole;
3-Bromo-5-fluoro-1-[4'-methoxy-3'-(1-methyl piperidin-4-yl oxy)benzenesulfonyl]-1H-indole;
3-Bromo-5-fluoro-1-[4'-ethyl-3'-(piperidin-4-yl oxy)benzenesulfonyl]-1H-indole hydrochloride.
5-Fluoro-1-[4'-ethyl-3'-(piperidin-4-yl oxy)benzenesulfonyl]-1H-indole hydrochloride;
3-Bromo-5-fluoro-1-[4'-ethyl-3'-(1-methyl piperidin-4-yl oxy)benzenesulfonyl]-1H-indole;
6-Bromo-1-[4'-ethyl-3'-(1-methyl piperidin-4-yl oxy)benzenesulfonyl]-1H-indole;
1-[4'-Ethyl-3'-(1-methyl piperidin-4-yl oxy)benzenesulfonyl]-1H-indole;
6-Chloro-1-[4'-ethyl-3'-(1-methyl piperidin-4-yl oxy)benzenesulfonyl]-1H-indole;
5-Fluoro-1-[4'-ethyl-3'-(1-methyl piperidin-4-yl oxy)benzenesulfonyl]-1H-indole;
5-Fluoro-3-methyl-1-[4'-isopropyl-3'-(1-methyl piperidin-4-yl oxy)benzenesulfonyl]-1H-indole;
5-Bromo-1-[4'-isopropyl-3'-(1-methyl piperidin-4-yl oxy) benzenesulfonyl]-1H-indole;
5-Bromo-1-[4'-Chloro-3'-(1-methyl piperidin-4-yl oxy)benzenesulfonyl]-1H-indole;
6-Methoxy-1-[4'-chloro-3'-(1-methyl piped din-4-yl oxy) benzenesulfonyl]-1H-indole;
5-Bromo-1-[4'-ethyl-3'-(1-methyl piperidin-4-yl oxy)benzenesulfonyl]-1H-indole;
6-Chloro-1-[3'-(1-methyl piperidin-4-yl oxy)benzenesulfonyl]-1H-indole;
6-Chloro-1-[4'-chloro-3'-(piperidin-4-yl oxy)benzenesulfonyl]-1H-indole hydrochloride;
4-Chloro-1-[4'-Methyl-3'-(N,N-dimethylamino propoxy) benzenesulfonyl]-1H-indole;
5-Methoxy-1-[3'-(N,N-dimethylamino ethoxy)benzenesulfonyl]-1H-indole;
1-[3'-(N,N-dimethylamino propoxy)benzenesulfonyl]-1H-indole;
1-[4'-Isopropyl-3'-(N,N-dimethylamino propoxy)benzenesulfonyl]-1H-indole;
5-Chloro-1-[4'-chloro-3'-(1-methyl piperidin-4-yl oxy)benzenesulfonyl]-1H-indole;
1-[4'-Chloro-3'-(1-methyl piperidin-4-yl oxy)benzenesulfonyl]-5-methoxy-3-methyl-1H-indole;
1-[4'-Ethyl-3'-(1-methyl piperidin-4-yl oxy)benzenesulfonyl]-5-fluoro-3-methyl 1H-indole;
a stereoisomer thereof; and a salt thereof.

DETAILED DESCRIPTION OF THE INVENTION

Unless otherwise stated, the following terms used in the specification and claims have the meanings given below:
"Halogen" means fluorine, chlorine, bromine or iodine;
"$(C_1-C_3)$alkyl" means straight or branched chain alkyl radicals containing one to three carbon atoms and includes methyl, ethyl, n-propyl and iso-propyl;
"$(C_1-C_3)$alkoxy" means straight or branched chain alkyl radicals containing one to three carbon atoms and includes methoxy, ethoxy, propyloxy and iso-propyloxy;
"Halo$(C_1-C_3)$alkyl" means straight or branched chain alkyl radicals containing one to three carbon atoms and includes fluoromethyl, difluoromethyl, trifluoromethyl, trifluoroethyl, fluoroethyl, difluoroethyl and the like;
"Halo$(C_1-C_3)$alkoxy" means straight or branched chain alkyl radicals containing one to three carbon atoms and includes fluoromethoxy, difluoromethoxy, trifluoromethoxy, trifluoroethoxy, fluoroethoxy, difluoroethoxy and the like;

"Cyclo$(C_3-C_6)$alkyl" means cyclic or branched cyclic alkyl radicals containing three to six carbon atoms and includes cyclopropyl, cyclobutyl, cyclopentyl or cyclohexyl, which may be substituted or unsubstituted and optionally the substituents may be selected from halogen, $(C_1-C_3)$alkyl or $(C_1-C_3)$alkoxy;
"Cyclo$(C_3-C_6)$alkoxy" means cyclic or branched cyclic alkyl radicals containing three to six carbon atoms and includes cyclopropyloxy, cyclobutyloxy, cyclopentyloxy or cyclohexyloxy.
"Cyclo alkyl$(C_3-C_6)$alkoxy" means cyclopropylmethyloxy, cyclobutylmethyloxy, cyclopentylmethyloxy or cyclohexylmethyloxy and the like;
"Heterocyclyl" means a non-aromatic saturated monocyclic or multicyclic ring system comprising about 3 to 10 ring atoms in which one or more of the atoms in the ring system is an element other than carbon, for example nitrogen, oxygen or sulfur, alone or in combination. Preferred heterocyclyls contain about 5 to 6 ring atoms. The prefix aza, oxa or thia before the heterocyclyl root name means that at least a nitrogen, oxygen or sulfur atom respectively is present as a ring atom. The heterocyclyl can be optionally substituted by replacing an available hydrogen on the ring by one or more substituents, which may be the same or different. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, pyranyl, tetrahydrothiophenyl, morpholinyl and the like The term "schizophrenia" means schizophrenia, schizophreniform, disorder, schizoaffective disorder and psychotic disorder wherein the term "psychotic" refers to delusions, prominent hallucinations, disorganized speech or disorganized or catatonic behavior. See Diagnostic and Statistical Manual of Mental Disorder, fourth edition, American Psychiatric Association, Washington, D.C.

The phrase "pharmaceutically acceptable" indicates that the substance or composition must be compatible chemically and/or toxicologically, with the other ingredients comprising a formulation, the mammal being treated therewith.

"Therapeutically effective amount" is defined as 'an amount of a compound of the present invention that (i) treats or prevents the particular disease, condition or disorder (ii) attenuates, ameliorates or eliminates one or more symptoms of the particular disease, condition or disorder (iii) prevents or delays the onset of one or more symptoms of the particular disease, condition, or disorder described herein'.

The terms "treating", "treat" or "treatment" embrace all the meanings such as preventative, prophylactic and palliative.

The term "stereoisomers" is a general term for all isomers of the individual molecules that differ only in the orientation of their atoms in space. It includes mirror image isomers (enantiomers), geometric (cis-trans) isomers and isomers of compounds with more than one chiral centre that are not mirror images of one another (diastereomers).

Certain compounds of formula (I) are capable of existing in stereoisomeric forms (e.g. diastereomers and enantiomers) and the invention extends to each of these stereoisomeric forms and to mixtures thereof including racemates. The different stereoisomeric forms may be separated from one another by the usual methods or any given isomer may be obtained by stereospecific or asymmetric synthesis. The invention also extends to tautomeric forms and mixtures thereof.

The stereoisomers as a rule are generally obtained as racemates that can be separated into the optically active isomers in a manner known per se. In the case of the compounds of general formula (I) having an asymmetric carbon atom the present invention relates to the D-form, the L-form and D,L-mixtures and in the case of a number of asymmetric carbon atoms, the diastereomeric forms and the invention extends to each of these stereo isomeric forms and to mixtures thereof including racemates. Those compounds of general formula (I) which have an asymmetric carbon and as a rule are obtained as racemates can be separated one from the other by the usual methods, or any given isomer may be obtained by stereo specific or asymmetric synthesis. However, it is also possible to employ an optically active compound from the start, a correspondingly optically active enantiomeric or diastereomeric compound then being obtained as the final compound.

The stereoisomers of compounds of general formula (I) may be prepared by one or more ways presented below:

i) One or more of the reagents may be used in their optically active form.

ii) Optically pure catalyst or chiral ligands along with metal catalyst may be employed in the reduction process. The metal catalyst may be Rhodium, Ruthenium, Indium and the like. The chiral ligands may preferably be chiral phosphines (Principles of Asymmetric synthesis, J. E. Baldwin Ed., Tetrahedron series, 14, 311-316).

iii) The mixture of stereoisomers may be resolved by conventional, methods such as forming diastereomeric salts with chiral acids or chiral amines, or chiral amino alcohols, chiral amino acids. The resulting mixture of diastereomers may then be separated by methods such as fractional crystallization, chromatography and the like, which is followed by an additional step of isolating the optically active product by hydrolyzing the derivative (Jacques et. al., "Enantiomers, Racemates and Resolution", Wiley Interscience, 1981).

iv) The mixture of stereoisomers may be resolved by conventional methods such as microbial resolution, resolving the diastereomeric salts formed with chiral acids or chiral bases.

Chiral acids that can be employed may be tartaric acid, mandelic acid, lactic acid, camphorsulfonic acid, amino acids and the like. Chiral bases that can be employed may be cinchona alkaloids, brucine or a basic amino acid such as lysine, arginine and the like. In the case of the compounds of general formula (I) containing geometric isomerism the present invention relates to all of these geometric isomers.

Suitable pharmaceutically acceptable salts will be apparent to those skilled in the art and include those described in J. Pharm. Sci., 1977, 66, 1-19, such as acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid. The present invention includes, within its scope, all possible stoichiometric and non-stoichiometric forms.

The pharmaceutically acceptable salts forming a part of this invention may be prepared by treating the compound of formula (I) with 1-6 equivalents of a base such as sodium hydride, sodium methoxide, sodium ethoxide, sodium hydroxide, potassium t-butoxide, calcium hydroxide, calcium acetate, calcium chloride, magnesium hydroxide, magnesium chloride and the like. Solvents such as water, acetone, ether, THF, methanol, ethanol, t-butanol, dioxane, isopropanol, isopropyl ether or mixtures thereof may be used.

In addition to pharmaceutically acceptable salts, other salts are included in the invention. They may serve as intermediates in the purification of the compounds, in the preparation of other salts, or in the identification and characterization of the compounds or intermediates.

The compounds of formula (I) may be prepared in crystalline or non-crystalline form, and, if crystalline, may optionally be solvated, eg. as the hydrate. This invention includes within its scope stoichiometric solvates (eg. hydrates) as well as compounds containing variable amounts of solvent (eg. water).

The present invention also provides a process for the preparation of a compound of formula (I) or a pharmaceutically acceptable salt thereof, which comprises of the following route, wherein the key intermediate is synthesized as described in preparations 1 to 3.

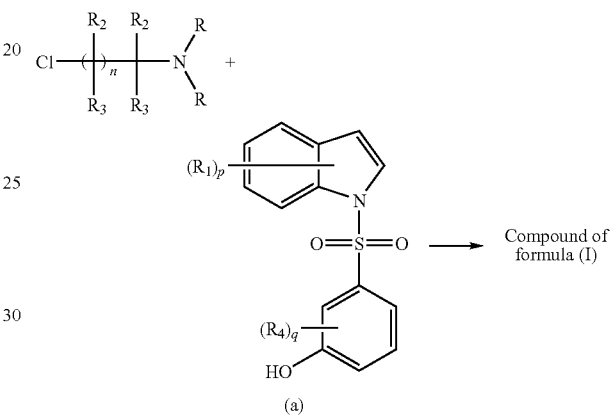

The process of this invention includes contacting a compound of the following formula (a),

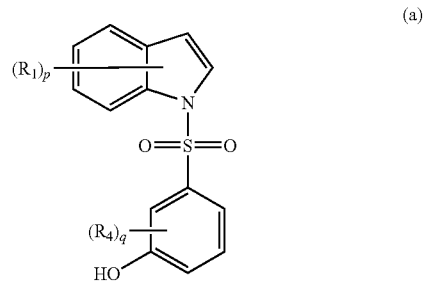

with amine derivatives, using a suitable base in presence of inert solvent at ambient temperature to obtain a compound of formula (I), wherein all substitutions are described as earlier.

The above reaction is preferably carried out in a solvent such as tetrahydrofuran (THF), toluene, ethyl acetate, water, dimethylformamide (DMF), dimethyl sulfoxide (DMSO), dimethyl ether (DME) and the like or a mixture thereof and preferably using DMF. The inert atmosphere may be maintained by using inert gases such as $N_2$, Ar or He. The reaction may be affected in the presence of a base such as potassium carbonate, sodium bicarbonate, sodium hydride or mixtures thereof. The reaction temperature may range from 20° C. to 150° C. based on the choice of solvent and preferably at a temperature in the range from 30° C. to 100° C. The duration of the reaction may range from 1 to 24 hours, preferably from a period of 2 to 6 hours.

The intermediate compound (a) can be obtained by reacting indole derivative with aryl sulfonyl chlorides ($ArSO_2Cl$); using suitable base in the presence of an inert solvent at suitable temperature. The solvent used in reaction can be selected from aromatic hydrocarbons such as toluene, o-, m-, p-xylene; halogenated hydrocarbons such as methylene chloride, chloroform, and chlorobenzene; ethers such as diethyl-ether, diisopropyl ether, tert-butyl methyl ether, dioxane, anisole, and tetrahydrofuran; nitriles such as acetonitrile and propionitrile; alcohols such as methanol, ethanol, n-propanol, n-butanol, tert-butanol and also DMF, DMSO and water. The preferred list of solvents include DMSO, DMF, acetonitrile and THF. Mixtures of these in varying ratios can also be used. The base used in reaction can be selected from inorganic compounds such as alkali metal hydroxides and alkaline earth metal hydroxides, such as lithium hydroxide, sodium hydroxide, potassium hydroxide and calcium hydroxide; alkali metal oxides and alkaline earth metal oxides, lithium oxide, sodium oxide, magnesium oxide and calcium oxide; alkali metal hydrides and alkaline earth metal hydrides such as lithium hydride, sodium hydride, potassium hydride and calcium hydride; alkali metal amides and alkaline earth metal amides such as lithium amide, sodium amide, potassium amide and calcium amide; alkali metal carbonates and alkaline earth metal carbonates such as lithium carbonate and calcium carbonate; and also alkali metal hydrogen carbonates and alkaline earth metal hydrogen carbonates such as sodium hydrogen carbonate; organometallic compounds, particularly alkali-metal alkyls such as methyl lithium, butyl lithium, phenyl lithium; alkyl magnesium halides such as methyl magnesium chloride and alkali metal alkoxides and alkaline earth metal alkoxides such as sodium methoxide, sodium ethoxide, potassium ethoxide, potassium tert-butoxide and di-methoxymagnesium, further more organic bases e.g. triethylamine, triisopropylamine, N-methylpiperidine and pyridine. Sodium hydroxide, sodium methoxide, sodium ethoxide, potassium hydroxide potassium carbonate and triethylamine are especially preferred. Suitably the reaction may be effected in the presence of phase transfer catalyst such as tetra-n-butylammonium hydrogensulphate and the like. The inert atmosphere may be maintained by using inert gases such as $N_2$, Ar or He. Reaction times may vary from 1 to 24 hrs, preferably from 2 to 6 hours, where after, if desired, the resulting compound is converted into a salt thereof.

Compounds obtained by the above method of preparation of the present invention can be transformed into another compound of this invention by further chemical modifications using well-known reactions such as oxidation, reduction, protection, deprotection, rearrangement reaction, halogenation, hydroxylation, alkylation, alkylthiolation, demethylation, O-alkylation, O-acylation, N-alkylation, N-alkenylation, N-acylation, N-cyanation, N-sulfonylation, coupling reaction using transition metals and the like.

If necessary, any one or more than one of the following steps can be carried out, i) Converting a compound of the formula (I) into another compound of the formula (I)

ii) Removing any protecting groups; or iii) Forming a pharmaceutically acceptable salt, solvate or a prodrug thereof.

Process (i) may be performed using conventional interconversion procedures such as epimerisation, oxidation, reduction, alkylation, nucleophilic or electrophilic aromatic substitution and ester hydrolysis or amide bond formation.

In process (ii) examples of protecting groups and the means for their removal can be found in T. W. Greene 'Protective Groups in Organic Synthesis' (J. Wiley and Sons, 1991). Suitable amine protecting groups include sulphonyl (e.g. tosyl), acyl (e.g. acetyl, 2',2',2'-trichloroethoxycarbonyl, benzyloxycarbonyl or t-butoxycarbonyl) and arylalkyl (eg. benzyl), which may be removed by hydrolysis (e.g. using an acid such as hydrochloric or trifluoroacetic acid) or reductively (e.g. hydrogenolysis of a benzyl group or reductive removal of a 2',2',2'-trichloroethoxycarbonyl group using zinc in acetic acid) as appropriate. Other suitable amine protecting groups include trifluoroacetyl, which may be removed by base catalysed hydrolysis or a solid phase resin bound benzyl group, such as a Merrifield resin bound 2,6-dimethoxybenzyl group (Ellman linker), which may be removed by acid catalyzed hydrolysis, for example with trifluoroacetic acid.

In process (iii) halogenation, hydroxylation, alkylation and/or pharmaceutically acceptable salts may be prepared conventionally by reaction with the appropriate acid or acid derivative as described earlier in detail.

In order to use the compounds of formula (I) in therapy, they will normally be formulated into a pharmaceutical composition in accordance with standard pharmaceutical practice.

The pharmaceutical compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol) and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampoules or in multi-dose containers, with an added preservative. The compositions may take such forms as suspensions, solutions or emulsions in oily or aqueous vehicles and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of an aerosol spray from a pressurized container or a nebulizer or from a capsule using a inhaler or insufflator. In the case of a pressurized aerosol, a suitable propellant, e.g., dichlorodifluoromethane, trichlorofluoromethane, dichlorotetrafluoroethane, carbon dioxide or other suitable gas and the dosage unit may be determined by providing a valve to deliver a metered amount. The medicament for pressurized container or nebulizer may contain a solution or suspension of the active compound while for a capsule, it preferably should be in the form of powder. Capsules and cartridges (made, for example, from gelatin) for use in an inhaler or insufflator may be formulated, containing a powder mix of a compound of the invention and a suitable powder base such as lactose or starch.

Aerosol formulations for treatment of the conditions referred to above (e.g., migraine) in the average adult human are preferably arranged so that each metered dose or "puff" of aerosol contains 20 µg to 1000 µg of the compound of the invention. The overall daily dose with an aerosol will be within the range 100 µg to 10 mg. Administration may be several times daily, for example 2, 3, 4 or 8 times, giving for example, 1, 2 or 3 doses each time.

An effective amount of a compound of general formula (I) or their derivatives as defined above can be used to produce a medicament, along with conventional pharmaceutical auxiliaries, carriers and additives.

Such therapy includes multiple choices: for example, administering two compatible compounds simultaneously in a single dose form or administering each compound individually in a separate dosage; or if required at same time interval or separately in order to maximize the beneficial effect or minimize the potential side-effects of the drugs according to the known principles of pharmacology.

The dose of the active compounds can vary depending on factors such as the route of administration, age and weight of patient, nature and severity of the disease to be treated and similar factors. Therefore, any reference herein to a pharmacologically effective amount of the compounds of general formula (I) refers to the aforementioned factors. A proposed dose of the active compounds of this invention, for either oral, parenteral, nasal or buccal administration, to an average adult human, for the treatment of the conditions referred to above, is 0.1 to 200 mg of the active ingredient per unit dose which could be administered, for example, 1 to 4 times per day.

For illustrative purposes, the reaction scheme depicted herein provides potential routes for synthesizing the compounds of the present invention as well as key intermediates. For a more detailed description of the individual reaction steps, see the Examples section. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in the light of this disclosure using conventional chemistry well known to those skilled in the art.

Commercial reagents were utilized without further purification. Room temperature refers to 25-30° C. IR were taken using KBr and in solid state. Unless otherwise stated, all mass spectra were carried out using ESI conditions. $^1$H-NMR spectra were recorded at 400 MHz on a Bruker instrument. Deuterated chloroform (99.8% D) was used as solvent. TMS was used as internal reference standard. Chemical shift-values are expressed in parts per million ($\delta$) values. The following abbreviations are used for the multiplicity for the NMR signals: s=singlet, bs=broad singlet, d=doublet, t=triplet, q=quartet, qui=quintet, h=heptet, dd=double doublet, dt=double triplet, tt=triplet of triplets, m=multiplet. Chromatography refers to column chromatography performed using 100-200 mesh silica gel and executed under nitrogen pressure (flash chromatography) conditions.

EXAMPLES

The novel compounds of the present invention were prepared according to the following procedures, using appropriate materials and are further exemplified by the following specific examples. The most preferred compounds of the invention are any or all of those specifically set forth in these examples. These compounds are not, however, to be construed as forming the only genius that is considered as the invention, and any combination of the compounds or their moieties may itself form a genus. The following examples further illustrate details for the preparation of the compounds of the present invention. Those skilled in the art will readily understand that known variations of the conditions and process of the following preparative procedures can be used to prepare these compounds.

Preparation 1: Preparation of 1-(3'-Hydroxy benzenesulfonyl)-1H-indole

Step (i): Preparation of 3-Nitrobenzenesulfonyl chloride

Chlorosulfonic acid (4.16 mmol, 0.475 grams) was taken in 1 L three neck round bottom flask equipped with a guard tube and liquid addition funnel. Chlorosulfonic acid was cooled in ice bath to 5-10° C. and nitrobenzene (0.83 mmol, 0.102 grams) was added to the acid slowly, at such a rate that the temperature maintained below 10° C. Reaction mixture was then brought to 25° C. and then slowly heated in an oil bath to 80-85° C. The above reaction mixture was stirred further at 80-85° C. for a period of 3 hours. After completion of the reaction, the reaction mixture was cooled to 10° C. and poured on to the ice-water mixture under stirring, while maintaining the temperature below 10° C. The resulting slurry was then filtered on buchner funnel. The solid cake was dried on phosphorous pentoxide in a desiccator to obtain the title compound as off white solid. Yield: 0.144 grams.

Step (ii): Preparation of 1-(3-Nitro benzenesulfonyl)-1H-indole

Indole (17.09 mmol, 2.0 grams) was taken in 1,2-dichloroethane (20 mL) in 100 mL three necked round-bottomed flask. Triethylamine (34.19 mmol, 3.45 grams) was added to it at 25° C. The above mixture was added to solution of 3-nitrobenzenesulfonyl chloride (25.64 mmol, 5.68 grams) (obtained from step (i)) and dichloromethane (25 mL), while maintaining the temperature below 10° C. The reaction mixture was then stirred for a period of 24 hours at 25° C. After the completion of reaction, the reaction mixture was poured onto ice-water mixture under stirring and the product was extracted with ethyl acetate (2×30 mL). The combined ethyl acetate extracts were then washed with water, brine and dried over anhydrous magnesium sulfate. The volatiles were removed under the reduced pressure to obtain 5.4 grams of thick syrupy mass, which was purified by column chromatography using silicagel (100-200 mesh), eluent being ethyl acetate and n-hexane (5:95),

Step (iii): Preparation of 1-(3-Amino benzenesulfonyl)-1H-indole 1-(3-Nitrobenzenesulfonyl)-1H-indole (obtained from step (ii)) (6.62 mmol, 2.0 grams) was taken in ethanol (10 mL) in a 50 mL three-necked round-bottomed flask. Iron powder, (33.11 mmol, 1.85 grams) was added to it at 25° C. followed by addition of water (2 mL) and 1-2 drops of hydrochloric acid. The reaction mixture was then stirred for a period of 4 hours at 75-80° C. After completion of the reaction, the reaction mixture was filtered through buchner funnel and solid mass on the filter was washed twice with hot ethanol (20 mL). Combined ethanol layer was concentrated under vacuum and the residual mass was poured onto ice-cold water (30 mL) and basified with 40% sodium hydroxide solution. Aqueous layer was extracted with dichloromethane (50 mL×3). The combined dichloromethane extracts were washed with water, brine and dried over anhydrous magnesium sulfate. The volatile substances were then removed tinder reduced pressure to obtain 2.4 grams thick syrupy mass which was purified by column chromatography using neutral silicagel (100-200 mesh), eluent being ethyl acetate and n-hexane (2:3).

Step (iv): Preparation of 1-(3-Hydroxy benzenesulfonyl)-1H-indole 1-(3-Aminobenzenesulfonyl)-1H-indole (obtained from step (iii)) (25.7 mmol, 7.0 grams) was taken in a 250 mL three-necked round-bottom flask. Water (80 mL) was added and the mixture was stirred for a period of 15 minutes at room temperature. Concentrated sulfuric acid was added drop wise (128.5 mmol, 7 mL) through dropping funnel and the reaction mass was stirred for a period of 15 minutes. Cooled the mass to 0-5° C. in an ice bath. Sodium nitrite (38.6 mmol, 2.72 grams) dissolved in water (3 mL) was added slowly and the reaction mixture was stirred at 0-5° C. for a period of one hour.

In another 500 mL flask, ice-cold water (50 mL) was taken and added concentrated sulfuric acid (50 mL) to it slowly in 10 minutes. The mass was warmed to 60-65° C. and added the above diazotized mass maintaining the temperature at 60-65° C. The resulting reaction mass was further stirred at 95-98° C. for a period of another 60 minutes. After completion of the reaction, the reaction mixture was poured onto ice water mixture under stirring and the resulting mixture was extracted with ethyl acetate (3×150 mL). The combined ethyl acetate extracts were then washed with water, brine and dried over anhydrous magnesium sulfate. The volatiles were removed under reduced pressure to obtain 7.33 grams of semisolid compound.

Preparation 2: Preparation of 6-Chloro-1-(3-hydroxy-4-methyl benzenesulfonyl)-1H-indole

Step (i): Preparation of N-acetyl-2-toluidine

Ortho toluidine (0.75 mol, 80 grams) was taken in a 1 L round bottom flask equipped with a liquid addition funnel and a guard tube. Triethylamine (1.13 mmol, 113.77 grams) was added to it in one lot. Above mixture was cooled to 0-5° C. and acetyl chloride (1.13 mmol, 88.7 grams) was added drop wise by maintaining the temperature below 10° C. After addition of acetyl chloride, cooling was removed and the reaction mass was stirred at 25-28° C. for a period of 3 hours. After completion of the reaction, the reaction mixture was poured onto 500 grams of ice-water and extracted with dichloromethane (2×300 mL). The combined dichloromethane extracts were then washed with water, brine and dried over anhydrous magnesium sulfate. The volatiles were removed under the reduced pressure to obtain 113.6 grams of solid product.

Step (ii): Preparation of 3-(N-Acetamido)-4-methyl benzenesulfonyl chloride

Chlorosulfonic acid (500 grams) was taken in a three neck round bottom flask equipped with a guard tube and cooled to 10° C. N-acetyl-2-toluidine (100 grams) (obtained from step (i)) was added in small portions while maintaining temperature below 10° C. Later the cooling was removed and reaction mixture was stirred at 25° C. for a period of 24 hours. After completion of the reaction, the reaction mixture was poured onto ice water, and the resulting slurry was filtered on Buchner funnel. Solid cake on funnel was washed with 500 mL of water and the resulting solid was dried on phosphorus pentoxide in desiccators to obtain 113.5 grams off white solid. The crude product was purified by crystallization from benzene and used for further experimentation.

Step (iii): Preparation of 6-Chloro-1-[3'-(N-acetamido)-4'-methyl benzenesulfonyl]-1H-indole Sodium hydride (132.0 mmol, 6.42 grams) was taken in tetrahydrofuran (20 mL), in a 500 mL three-necked round-bottomed flask under nitrogen atmosphere and cooled to 5° C. To this mixture, 6-chloroindole (66.0 mmol, 10 grams) dissolved in tetrahydrofuran (50 mL) was added slowly. Then the reaction mixture was brought to room temperature and stirred for a period of one hour. The reaction mixture was cooled to 10° C. and 3-acetamido-4-methyl benzenesulfonyl chloride (99.0 mmol, 24.60 grams) (obtained from step (ii)) was added in lots. After completion of the addition, the reaction mixture was gradually brought to room temperature and maintained over night. After completion of the reaction, tetrahydrofuran was distilled off from the reaction mixture. The concentrated reaction mixture was then poured onto water under stirring and the resulting mixture was extracted with ethyl acetate (4×150 mL). The combined ethyl acetate extracts were washed with water, brine and dried over anhydrous sodium sulfate. The volatiles were removed under the reduced pressure to obtain 22 grams of thick syrupy mass. The compound was purified by column chromatography using silica gel (100-200 mesh size), eluent being ethyl acetate and n-hexane (1:3) to obtain 7.66 grams of the product.

Step (iv): Preparation of 6-Chloro-1-(3'-amino-4'-methyl benzenesulfonyl)-1H-indole 6-Chloro-1-[(3'-(N-acetamido)-4'-methyl)benzenesulfonyl]-1H-indole (21.1 mmol, 7.66 grams) (obtained from step (iii)) was taken in a 250 mL three-necked round bottom flask and added ethanol (80 mL). The resulting solution was heated on water bath to 50-55° C. and hydrochloric acid (52.8 mmol, 6.42 grams) was added drop-wise. Reaction mixture was refluxed at 80-85° C. for a period of 3 hours. After completion of the reaction, ethanol was distilled off from reaction mixture and the concentrated reaction mixture was poured onto water (150 mL). The product was extracted with ethyl acetate (4×50 mL). The combined ethyl acetate extracts were then washed with water, brine and dried over anhydrous magnesium sulfate. The volatiles were removed under reduced pressure to obtain 6.72 grams thick syrupy mass. The compound was purified by column chromatography using silica gel (100-200 mesh), eluent being ethyl acetate and hexane (1:9) to obtain 1.32 grams of pure compound.

Step (v): Preparation of 6-Chloro-1-(3'-hydroxy-4'-methyl benzenesulfonyl)-1H-indole 6-Chloro-1-(3-amino-4-methyl)benzenesulfonyl-1H-indole (8.48 mmol, 2.72 grams) (obtained from step (iv)) was diazotized as described previously in step (iv) of preparation 1. The compound was purified by column chromatography using silica gel (100-200 mesh size), the eluent being ethyl acetate and hexane (3:97) to obtain 0.76 grams of pure compound.

Preparation 3: Preparation of 1-(3'-Hydroxy-4'-ethyl benzenesulfonyl)-1H-indole

Step (i): Preparation of 2-Ethylacetanilide

2-Ethylaniline (82.6 mmol, 10 gams) was taken in round bottom flask equipped with a liquid addition funnel and a guard tube. Triethylamine (165 mmol, 16.69 grams) was added to it in one lot. The mass, thus obtained, was cooled to 0-5° C. and added acetyl chloride (123 mmol, 9.73 grams) drop wise, while maintaining the mass temperature below 10° C. After addition of acetyl chloride, cooling was removed and reaction was stirred at 25-28° C. for a period of 3 hours. After completion of the reaction, the reaction mixture was poured onto 200 mL of ice water and aqueous layer was extracted with dichloromethane (2×100 mL). The combined dichloromethane extracts were then washed with water, brine and dried over anhydrous magnesium sulfate. The volatiles were removed under the reduced pressure to obtain 14.09 grams of compound.

Step (ii): Preparation of 3-(N-Acetamido)-4-ethyl benzenesulfonyl chloride

Chlorosulfonic acid (426 mmol, 49.63 grams) was taken in a 500 mL three neck round bottom flask equipped with a guard tube and cooled to 10° C. 2-Ethylacetanilide (85.2 mmol, 13.89 grams) (obtained from step (i)) was added in small portions while maintaining temperature below 10° C. After complete addition of 2-Ethylacetanilide, cooling was removed and reaction was stirred at room temperature for a further period of 24 hours. After completion of the reaction, the reaction mixture was poured onto ice water under stirring and the resulting mixture was extracted with ethyl acetate (3×150 mL). The combined ethyl acetate extracts were then washed with water, brine and dried over anhydrous magnesium sulfate. The volatiles were removed under the reduced pressure to obtain 17.51 grams of the compound.

Step (iii): Preparation of 1-[3'-(N-Acetamido)-4'-ethyl benzenesulfonyl]-1H-indole Sodium hydride (132.0 mmol, 6.42 grams) was taken in tetrahydrofuran (20 mL), in three-necked round-bottomed flask under nitrogen atmosphere and cooled to 5° C. To this mixture, 6-chloroindole (66.0 mmol, 10 grams) dissolved in tetrahydrofuran (50 mL) was added slowly. Then the reaction mixture was brought to room temperature and stirred for a period of one hour. The above reaction mixture was cooled to 10° C. and 3-acetamido-4-ethylbenzenesulfonyl chloride (56.5 mmol, 16.41 grams) (obtained from step (ii)) was added in lots. After completion of the addition, the reaction mixture was gradually brought to room temperature. Tetrahydrofuran was distilled off from reaction mixture and the concentrated reaction mass was poured onto water with stirring. The resulting mixture was extracted with ethyl acetate (4×150 mL). The combined ethyl acetate extracts were washed successively with water, brine and dried over anhydrous sodium sulfate. The volatiles were removed under the reduced pressure to obtain 22 grams thick syrup mass. The compound was purified by column chromatography using silica gel (100-200 mesh); eluent being ethyl acetate and n-hexane (1:3) to obtain 7.66 grams of the compound.

Step (iv): Preparation of 1-(3'-Amino-4'-ethyl benzenesulfonyl)-1H-indole

3'-Acetamido-4'-ethyl benzenesulfonyl indole (7.16 mmol, 2.5 grams) (obtained from step (iii)) was taken in a 250 mL three necked round bottom flask in ethanol (80 mL). Above solution was heated on water bath to 50-55° C. and hydrochloric acid (52.8 mmol, 6.42 grams, 30% purity) was added drop wise. The resulting mixture was refluxed at 80-85° C. for a period of 3 hours. After completion of the reaction, ethanol was distilled off from the reaction mixture and the concentrated, reaction mixture was poured on to water (150 mL) and extracted with ethyl acetate (4×50 mL). The combined ethyl acetate extracts were then washed with water, brine and dried over anhydrous magnesium sulfate. The volatiles were removed under reduced pressure to obtain 6.72 grams of thick syrupy mass. The compound was purified by column chromatography using silica gel (100-200 mesh), eluent being ethyl acetate and n-hexane (1:9) to obtain 1.32 grams of the compound.

Step (v): Preparation of 1-(3-Hydroxy-4-ethyl benzenesulfonyl)-1H-indole 1-(3'-Amino-4'-ethyl benzenesulfonyl) indole (2.99 mmol, 0.909 grams) (obtained from step (iv)) was taken in a 250 mL three-necked round bottom flask. Water (80 mL) was added to the above compound and the mixture was stirred for a period of 15 minutes at room temperature. Concentrated sulfuric acid was added drop wise (128.5 mmol, 7 mL) through dropping funnel and the reaction mass was stirred for another 15 minutes. Then the reaction mass was cooled to 0-5° C. with an ice bath. Sodium nitrite (38.6 mmol, 2.72 grams) dissolved in water (3 mL) was added slowly and the reaction mixture was stirred at 0-5° C. for a period of one hour.

In another 500 mL flask, containing ice-cold water (50 mL), concentrated sulfuric acid (50 mL) was added slowly in 10 minutes. Then the mass was warmed to 60-65° C. and added the above diazotized mass maintaining the mass temperature 60-65° C. The resulting reaction mass was stirred at 95-98° C. for another 60 minutes. After the completion of the reaction, the reaction mixture was poured onto ice-water under stirring and the resulting mixture was extracted with ethyl acetate (3×150 mL). The combined ethyl acetate extracts were then washed with water, brine and dried over anhydrous magnesium sulfate. The volatiles were removed under the reduced pressure to obtain 0.221 grams crude semi-solid compound.

Example 1

Preparation of 1-[3'-(N,N-dimethylamino ethoxy)benzenesulfonyl]-1H-indole 1-(3'-Hydroxybenzenesulfonyl) indole (0.602 mmol, 0.163 grams) (obtained from preparation 1) was taken in 50 mL two neck round bottom flask and added tetrahydrofuran (7 mL). To the above mixture potassium carbonate (1.24 mmol, 0.171 grams) was added and stirred for a period of 15-20 minutes. The free base generated from 2-dimethylaminoethyl chloride hydrochloride (2.48 mmol, 0.358 grams), by dissolving it in a solution of 3 mL 40% aqueous sodium hydroxide, diluted with 5 mL water and extracting free base with toluene (3 mL) was directly charged to reaction mixture. Reaction mixture was kept on reflux temperature and the progress was monitored. After completion of reaction, the reaction mass was cooled to room temperature, poured onto 25 mL of water and extracted the product with ethyl acetate (10 mL×4). Combined organic extracts were dried over sodium sulfate and the volatiles were removed under the reduced pressure to obtain 0.214 grams crude compound. The compound was purified by column chromatography using silica gel (100-200 mesh), the eluents being ethyl acetate and n-hexane (2:3) to obtain pure compound.

IR (cm$^{-1}$): 2947, 1373, 1170;
$^1$H-NMR (ppm): 2.32 (6H, s), 2.70-2.73 (2H, t, J=5.57 Hz), 4.00-4.03 (2H, t, J=5.58 Hz), 6.66-6.67 (1H, d, J=333 Hz), 7.04-7.07 (1H, m); 7.20-7.24 (1H, m), 7.28-7.33 (2H, m), 7.37-7.38 (1H, m), 7.43-7.48 (1H, m), 7.52-7.54 (1H, d, J=7.94 Hz), 7.54-7.55 (1H, d, J=3.76 Hz), 7.97-7.99 (1H, d, J=8.29 Hz);
Mass (m/z): 345 (M+H)$^+$.

Example 2

Preparation of 5-Fluoro-1-[3'-(N,N-dimethylamino ethoxy)benzenesulfonyl]-1H-indole Using a similar procedure as given in the Example 1, with some non-critical variations the above derivative was prepared.

IR (cm$^{-1}$): 2945, 1374, 1175;
$^1$H-NMR (ppm): 2.32 (6H, s), 2.70-2.72 (2H, t, J=5.53 Hz), 4.00-4.03 (2H, t, J=5.57 Hz), 6.62-6.63 (1H, d, J=3.51 Hz), 7.01-7.04 (2H, m), 7.16-7.19 (1H, dd, J=8.72, 2.53 Hz), 7.31-7.33 (1H, d, J=7.96 Hz), 7.35-7.36 (1H, dd, J=2.14 Hz), 7.41-7.43 (1H, m), 7.57-7.58 (1H, d, J=3.66 Hz), 7.90-7.94 (1H, dd, J=9.04, 4.4 Hz);
Mass (m/z): 363 (M+H)$^+$.

Example 3

Preparation of 5-Bromo-1-(3'-[N,N-dimethylamino ethoxy)benzenesulfonyl]-1H-indole Using a similar procedure as given in the Example 1, with some non-critical variations the above derivative was prepared.

IR (cm$^{-1}$): 2947, 1373, 1170;
$^1$H-NMR (ppm): 2.32 (6H, s), 2.70-2.73 (2H, t, J=5.6 Hz), 4.01-4.03 (2H, q, J=5.6 Hz), 6.59-6.60 (1H, d, J=3.71 Hz), 7.06-7.09 (1H, m), 7.31-7.33 (1H, d, J=7.96 Hz), 7.35-7.36 (1H, m); 7.39-7.43 (2H, m), 7.54-7.55 (1H, d, J=3.65 Hz), 7.66-7.67 (1H, d, J=1.88 Hz), 7.84-7.87 (1H, d, J=8.82 Hz);
Mass (m/z): 423, 425 (M+H)$^+$.

Example 4

Preparation of 5-Fluoro-1-[3'-(N,N-dimethylamino propoxy)benzenesulfonyl]-1H-indole 5-Fluoro-1-(3-hydroxybenzenesulfonyl) indole was treated in a similar procedure as given in the Example 1 with 3-dimethylaminopropylchloride hydrochloride (2.48 mmol, 0.393 grams), with some non-critical variations to obtain the above derivative.

IR (cm$^{-1}$): 2946, 1374, 1175;
$^1$H-NMR (ppm): 1.90-1.97 (2H, m), 2.25 (6H, s), 2.42-2.46 (2H, t, J=7.08 Hz), 3.96-3.99 (2H, t, J=6.36 Hz), 6.62-6.63 (1H, d, J=3.44 Hz), 7.03-7.06 (2H, m), 7.18-7.28 (1H, dd), 7.30-7.32 (1H, d, J=8 Hz), 7.33-7.39 (2H, m), 7.58-7.59 (1H, d, J=3.6 Hz), 7.90-7.94 (1H, dd, J=9.0, 4.4 Hz);
Mass (m/z): 377 (M+H)$^+$.

Example 5

Preparation of 5-Bromo-1-[3'-(N,N-dimethylamino propoxy)benzenesulfonyl]-1H-indole Using a similar procedure as given in the Example 4, with some non-critical variations the above derivative was prepared.

IR (cm$^{-1}$): 2947, 1373, 1170;
$^1$H-NMR (ppm): 1.89-1.97 (2H, m), 2.25 (6H, s), 2.40-2.44 (2H, t, J=7.08 Hz), 3.96-3.99 (2H, t, J=6.41 Hz), 6.60-6.61 (1H, d, J=3.54 Hz), 7.04-7.06 (1H, m), 7.30-7.34 (2H, m), 7.38-7.42 (2H, m), 7.55-7.56 (1H, d, J=3.7 Hz), 7.66-7.67 (1H, d, J=1.85 Hz), 7.85-7.87 (1H, d, J=8.82 Hz);
Mass (m/z): 437, 439 (m+n)$^+$.

Example 6

Preparation of 1-[3'-(N,N-Dimethylamino propoxy)benzenesulfonyl]-5-methoxy-1H-indole Using a similar procedure as given in the Example 4, with some non-critical variations the above derivative is prepared.

IR (cm$^{-1}$): 2948, 1373, 1170;
$^1$H-NMR (ppm): 1.88-1.99 (2H, m), 2.24 (6H, s), 2.40-2.44 (2H, t, J=7.09 Hz), 3.81 (3H, s), 3.95-3.98 (2H, t, J=6.37 Hz), 6.58-6.59 (1H, d, J=3.70 Hz), 6.91-6.94 (1H, dd, J=9.0, 2.5 Hz), 6.96-6.97 (1H, d, J=2.43 Hz), 7.01-7.03 (1H, m), 7.27-7.40 (3H, m), 7.50-7.51 (1H, d, J=3.60 Hz), 7.86-7.89 (1H, d, J=9.01 Hz);
Mass (m/z): 389 (M+H)$^+$.

Example 7

Preparation of 1-[3'-(1-Methylpiperidin-4-yl oxy)benzenesulfonyl]-1H-indole 1-(3'-Hydroxybenzenesulfonyl) indole, (0.36 mmol, 0.1 grams) (obtained from preparation 1), was dissolved in dimethyl sulfoxide (2 mL). Potassium carbonate (0.074 grams) was added and the resulting reaction mixture was stirred 40-45° C. for a period of one hour. In another round bottom flask, 4-chloro-N-methylpiperidine (0.54 mmol, 0.072 grams) was dissolved in dimethyl sulfoxide (1.5 mL). The content of the first flask were added to the second flask at 40-45° C. The resulting reaction mass was further heated to 140-145° C. and maintained there for a period of 5 hours while monitoring the reaction by thin layer chromatography. Cooled the reaction mass to room temperature, poured it onto water (25 mL) and extracted the product with ethyl acetate (30 mL×3). Combined organic extracts were dried over sodium sulfate and the volatiles were removed under the reduced pressure to obtain 0.110 grams crude compound. The compound was purified by column chromatography using silica gel (100-200 mesh), eluent being ethyl acetate and 1% triethylamine to obtain 50 mg of pure compound.

IR (cm$^{-1}$): 2933, 1595, 1445, 1372, 1173;

1H-NMR (ppm): 1.73-1.79 (2H, m), 1.90-2.05 (2H, m), 2.17 (2H, m), 2.31 (3H, s), 2.64-2.66 (2H, m), 4.32 (1H, m), 6.66-6.67 (1H, d, J=3.72 Hz), 7.01-7.03 (1H, dd, J=8.24, 2.36 Hz), 7.23-7.29 (1H, m), 7.29-7.33 (4H, m), 7.52-7.54 (2H, m), 7.99-8.01 (1H, d, J=8.28 Hz);

Mass (m/z): 371.2 (M+14)$^+$.

Example 8

Preparation of 5-Fluoro-1-[3'-(1-methylpiperidin-4-yl oxy)benzenesulfonyl]-1H-indole Using a similar procedure as given in the Example 7, with some non-critical variations the above derivative was prepared.

IR (cm$^{-1}$): 2933, 1445, 1373, 1172;

$^1$H-NMR (ppm): 1.80-1.85 (2H, m), 2.02-2.05 (2H, m), 2.39 (3H, s), 2.56-2.57 (2H, m), 2.71-2.73 (2H, m), 4.36 (1H, m), 6.22-6.31 (1H, d, J=3.60 Hz), 7.01-7.05 (2H, m), 7.16-7.19 (1H, dd, J=8.8, 2.5 Hz), 7.28-7.29 (1H, t, J=2.0 Hz), 7.32=7.34 (1H, d, J=8.0 Hz), 7.39-7.41 (1H, d, J=3.6 Hz), 7.56-7.57 (1H, d, J=3.6 Hz), 7.90-7.94 (1H, m);

Mass (m/z): 389.3 (M+H)$^+$.

Example 9

Preparation of 5-Methoxy-1-[3'-(1-methylpiperidin-4-yl oxy)benzenesulfonyl]-1H-indole Using a similar procedure as given in the Example 7, with some non-critical variations the above derivative was prepared.

IR (cm$^{-1}$): 2933, 1445, 1373, 1172;

$^1$H-NMR (ppm): 1.76-1.80 (2H, m), 1.93-1.98 (2H, m), 2.35 (3H, s) 2.38-2.42 (2H, m), 2.65-2.75 (2H, m), 3.81 (3H, s), 4.29-4.30 (1H, m), 6.58-6.60 (1H, d, J=3.60 Hz), 6.91-6.94 (1H, d, J=8.96 Hz), 6.97 (1H, d, J=2.44 Hz), 7.28-7.29 (2H, m), 7.30-7.32 (1H, d, J=8.12 Hz), 7.38 (1H, m), 7.48-7.49 (1H, d, J=3.6 Hz), 7.87-7.89 (1H, d, J=9 Hz);

Mass (m/z): 401.3 (MH-H)$^+$.

Example 10

Preparation of 1-[4'-Methyl-3'-(N,N-dimethylamino ethoxy)benzenesulfonyl]-1H-indole Using a similar procedure as given in the Example 1 and 1-(3-Hydroxy-4-methyl)benzenesulfonyl-1H-indole (obtained from preparation 2), with some non-critical variations the above derivative was prepared.

IR (cm$^{-1}$): 2944, 1372, 1177;

$^1$H-NMR (ppm): 2.17 (3H, s), 2.33 (6H, s), 2.70-2.73 (2H, t, J=5.68 Hz), 4.01-4.03 (2H, t, J=5.72 Hz), 6.64-6.65 (1H, d, J=3.6 Hz), 7.14-7.16 (1H, d, J=7.88 Hz), 7.21-7.30 (3H, m), 7.36-7.38 (1H, dd, J=7.84, 1.76 Hz), 7.51-7.53 (1H, d, J=7.8 Hz), 7.54-7.55 (1H, d, J=3.72 Hz), 7.97-8.00 (1H, d, J=8.28 Hz);

Mass (m/z): 359.4 (M+H)$^+$.

Example 11

Preparation of 5-Fluoro-1-[4'-methyl-3'-(N,N-dimethylamino ethoxy)benzenesulfonyl]-1H-indole Using a similar procedure as given in the Example 10, with some non-critical variations the above derivative was prepared.

IR (cm$^{-1}$): 2944, 1372, 1172, 1138;

$^1$H-NMR (ppm): 2.18 (3H, s), 2.33 (6H, s), 2.72-2.74 (2H, t, J=5.68 Hz), 4.01-4.03 (2H, t, J=5.72 Hz), 6.60-6.61 (1H, d, J=3.6 Hz), 7.02-7.03 (1H, dt, J=2.52), 7.15-7.18 (2H, m), 7.20 (1H, d, J=1.68 Hz), 7.34-7.36 (1H, dd, J=7.84, 1.76 Hz), 7.57-7.58 (1H, d, J=3.68 Hz), 7.90-7.92 (1H, q, J=4.64 Hz);

Mass (m/z): 377.3 (M+H)$^+$.

Example 12

Preparation of 5-Bromo-1-[4'-methyl-3'-(N,N-dimethylamino ethoxy)benzenesulfonyl]-1H-indole Using a similar procedure as given in the Example 10, with some non-critical variations the above derivative was prepared.

IR (cm$^{-1}$): 2939, 1369, 1171;

$^1$H-NMR (ppm): 2.18 (3H, s), 2.38 (6H, s), 2.74-2.76 (2H, t, J=5.48 Hz), 4.02-4.05 (2H, t, J=5.64 Hz), 6.58-6.59 (1H, d, J=192 Hz), 7.15-7.17 (1H, d, J=7.92 Hz), 7.20 (1H, d, J=1.72 Hz), 7.34-7.36 (1H, dd, J=7.84, 1.76 Hz), 7.38-7.41 (1H, dd, J=8.8, 1.92 Hz), 7.54-7.55 (1H, d, J=3.64 Hz), 7.65-7.66 (1H, d, J=1.88 Hz), 7.84-7.87 (1H, d, J=8.8 Hz);

Mass (m/z): 437, 439 (M+H)$^+$.

Example 13

Preparation of 1-[4'-Methyl-3'-(N,N-dimethylamino ethoxy)benzenesulfonyl]-5-methoxy-1H-indole Using a similar procedure as given in the Example 10, with some non-critical variations the above derivative was prepared.

IR (cm$^{-1}$): 2944, 1373, 1170;

$^1$H-NMR (ppm): 2.17 (3H, s), 2.34 (6H, s), 2.72-2.75 (2H, t, J=5.66 Hz), 3.80 (3H, s), 4.01-4.04 (2H, t, J=5.68 Hz), 6.57 (1H, d, J=3.57 Hz), 6.90-6.93 (1H, dd, J=9.0, 2.47 Hz), 6.96 (1H, d, J=2.44 Hz), 7.13-7.15 (1H, d, J=7.88 Hz), 7.20 (1H, d, J=1.67 Hz), 7.33-7.35 (1H, dd, J=7.85, 1.75 Hz), 7.49-7.50 (1H, d, J=3.62 Hz), 7.86-7.88 (1H, d, J=8.96 Hz);

Mass (m/z): 389.4 (M+H)$^+$.

Example 14

Preparation of 5-Ethoxy-1-[4'-methyl-3'-(N,N-dimethylamino ethoxy)benzenesulfonyl]-1H-indole Using a similar procedure as given in the Example 10, with some non-critical variations the above derivative was prepared.

IR (cm$^{-1}$): 2947, 1373, 1170;

$^1$H-NMR (ppm): 1.38-1.42 (31-1, t, J=6.96 Hz), 2.17 (3H, s), 2.37 (6H, s), 2.75-2.80 (2H, t, J=5.56 Hz), 3.99-4.02 (2H, q, J=6.96 Hz), 4.03-4.06 (2H, t, J=5.6 Hz), 6.55-6.56 (1H, d, J=3.68 Hz), 6.89-6.92 (1H, dd, J=9.0, 2.48 Hz), 6.94-6.95 (1H, d, J=2.4 Hz), 7.13-7.15 (1H, d, J=7.88 Hz), 7.19-7.20

(1H, d, J=1.56 Hz), 7.33-7.35 (1H, dd, J=7.84, 1.64 Hz), 7.48-7.49 (1H, d, J=3.6 Hz), 7.85-7.87 (1H, d, J=9.08 Hz);
Mass (m/z): 403 (M+H)$^+$.

Example 15

Preparation of 6-Chloro-1-[4'-methyl-3'-(N,N-dimethylamino ethoxy)benzenesulfonyl]-1H-indole Using a similar procedure as given in the Example 10, with some non-critical variations the above derivative was prepared.
IR (cm$^{-1}$): 1371, 1172, 1137;
$^1$H-NMR (ppm): 2.19 (3H, s), 2.38 (6H, s), 2.80-2.83 (2H, t, J=5.56 Hz), 4.0-4.10 (2H, t, J=5.56 Hz), 6.61-6.62 (1H, d, J=3.68 Hz). 7.17-7.21 (2H, m), 7.24-7.25 (1H, d, J=1.72 Hz), 7.36-7.38 (1H, dd, J=7.88, 1.76 Hz), 7.42-7.44 (1H, d, J=8.4 Hz), 7.53-7.54 (1H, d, J=3.64 Hz), 8.01-8.02 (1H, d, J=1.68 Hz);
Mass (m/z): 393.5 (M+H)$^+$.

Example 16

Preparation of 1-[4'-Methyl-3'-(N,N-dimethylamino propoxy)benzenesulfonyl]-1H-indole 1-(3-Hydroxy-4-methyl)benzenesulfonyl-1H-indole (0.622 mmol, 0.2 grams) (obtained from preparation 2) was dissolved in tetrahydrofuran (7 mL). To the above mixture, potassium carbonate (1.024 mmol, 0.171 grams) was added and stirred for a period of 15-20 minutes. The free base generated from 3-dimethylaminopropylchloride hydrochloride (2.48 mmol, 0.393 grams) was extracted with toluene (3 mL) and directly charged into the reaction mixture. The reaction mixture was refluxed while monitoring the progress of the reaction. After completion of reaction, the mass was cooled to room temperature and poured it on to water (25 mL) and extracted the product with ethyl acetate (10 mL×4). Combined organic extracts dried over sodium sulfate and the volatiles were removed under the reduced pressure to obtain 0.219 grams of crude compound. The compound was purified by column chromatography using silica gel (100-200 mesh) to obtain 0.143 grams of pure compound.
IR (cm$^{-1}$): 2944, 1373, 1171;
$^1$H-NMR (ppm): 1.91-1.98 (2H, m), 2.16 (3H, s), 2.26 (6H, s), 2.43-2.46 (2H, t, J=7.12 Hz), 3.96-3.99 (2H, t, J=6.24 Hz), 6.64-6.65 (1H, d, J=3.68 Hz), 7.13-7.15 (1H, d, J=7.88 Hz), 7.22-7.30 (3H, m), 7.34-7.37 (1H, dd, J=7.84, 1.76 Hz), 7.51-7.53 (1H, d, J=7.8 Hz), 7.55 (1H, d, J=3.72 Hz), 7.98-8.00 (1H, d, J=8.28 Hz);
Mass (m/z): 373 (M+H)$^+$.

Example 17

Preparation of 5-Fluoro-1-[4'-Methyl-3'-(N,N-dimethylamino propoxy)benzenesulfonyl]-1H-indole Using a similar procedure as given in the Example 16, with some non-critical variations the above derivative was prepared.
IR (cm$^{-1}$): 2947, 2860, 1373, 1171, 1137;
$^1$H-NMR (ppm): 1.92-1.98 (2H, m), 2.17 (3H, s), 2.25 (6H, s), 2.42-2.46 (2H, t, J=7.36 Hz), 3.96-3.99 (2H, t, J=6.28 Hz), 6.60-6.61 (1H, d, J=3.48 Hz, 7.03-7.16 (1H, dt, J=2.52 Hz), 7.18 (2H, m), 7.21 (1H, d, J=1.76 Hz), 7.32-7.34 (1H, dd, J=7.84, 1.8 Hz), 7.57-7.58 (1H, d, J=3.64 Hz), 7.91-7.92 (1H, dd, J=4.4 Hz);
Mass (m/z): 391.4 (M+H)$^+$.

Example 18

Preparation of 5-Bromo-1-[4'-Methyl-3'-(N,N-dimethylamino propoxy)benzenesulfonyl]-1H-indole Using a similar procedure as given in the Example 16, with some non-critical variations the above derivative was prepared.
IR (cm$^{-1}$): 2948, 1374, 1168;
$^1$H-NMR (ppm): 1.93-2.00 (2H, m), 2.18 (3H, s), 2.27 (6H, s), 2.44-2.48 (2H, t, J=7.12 Hz), 3.96-3.99 (2H, t, J=6.24 Hz), 6.58-6.59 (1H, d, J=3.84 Hz), 7.15-7.17 (1H, d, J=7.92 Hz), 7.20-7.21 (1H, d, J=1.72 Hz), 7.32-7.34 (1H, dd, J=7.88, 1.8 Hz), 738-7.41 (1H, dd, J=8.8, 1.96 Hz), 7.55-7.56 (1H, d, J=3.64 Hz), 7.65-7.66 (1H, d, J=1.84 Hz), 7.85-7.87 (1H, d, J=8.8 Hz);
Mass (m/z): 451, 453 (M+H)$^+$.

Example 19

Preparation of 1-[4'-Methyl-3'-(N,N-dimethylamino propoxy)benzenesulfonyl]-5-methoxy-1H-indole Using a similar procedure as given in the Example 16, with some non-critical variations the above derivative was prepared.
IR (cm$^{-1}$): 2944, 1373, 1173;
$^1$H-NMR (ppm): 1.90-1.94 (2H, m), 2.16 (3H, s), 2.25 (6H, s), 2.41-2.45 (2H, t, J=7.08 Hz), 3.80 (3H, s), 3.95-3.98 (2H, t, J=6.2 Hz), 6.57-6.58 (1H, s, J=3.56 Hz), 6.90-6.93 (1H, dd, J=9.04, 2.48 Hz), 6.96 (1H, d, J=2.44 Hz), 7.12-7.14 (1H, d, J=7.88 Hz), 7.21 (1H, d, J=1.68 Hz), 7.31-7.33 (1H, dd, J=7.84, 1.76 Hz), 7.50 (1H, d, J=3.6 Hz), 7.86-7.89 (1H, d, J=9 Hz);
Mass (m/z): 403.5 (M+H)$^+$.

Example 20

Preparation of 5-Ethoxy-1-[4'-methyl-3'-(N,N-dimethylamino propoxy)benzenesulfonyl]-1H-indole Using a similar procedure as given in the Example 16, with some non-critical variations the above derivative was prepared.
IR (cm$^{-1}$): 2948, 1373, 1170;
$^1$H-NMR (ppm): 1.39-1.42 (3H, t, J=6.92 Hz), 1.98-2.06 (2H, m), 2.16 (3H, s), 2.35 (6H, s), 2.57-2.61 (2H, t, J=7.32 Hz), 3.95-3.98 (2H, t, J=6.10 Hz), 3.99-4.04 (2H, q, J=6.99 Hz), 6.56-6.57 (1H, d, J=3.47 Hz), 6.90-6.93 (1H, dd, J=8.95, 2.47 Hz), 6.95 (1H, d, J=2.35 Hz), 7.12-7.14 (1H, d, J=7.89 Hz), 7.18-7.19 (1H, d, J=1.67 Hz), 7.32-7.34 (1H, dd, J=7.87, 1.73 Hz), 7.49 (1H, d, J=3.63 Hz), 7.85-7.87 (1H, d, J=8.88 Hz);
Mass (m/z): 417 (M+H)$^+$.

Example 21

Preparation of 6-Chloro-1-[4'-methyl-3'-(N,N-dimethylamino propoxy)benzenesulfonyl]-1H-indole Using a similar procedure as given in the Example 16, with some non-critical variations the above derivative was prepared.
IR (cm$^{-1}$): 1371, 1172, 1137;

¹H-NMR (ppm): 2.0-2.10 (2H, m), 2.18 (3H, s), 2.40 (6H, s), 2.66-2.70 (2H, t, J=7.48 Hz), 3.99-4.0 (2H, t, J=6.12 Hz), 6.61-6.62 (1H, d, J=3.64 Hz), 7.17-7.21 (2H, m), 7.22-7.23 (1H, d, J=1.68 Hz), 7.35-7.37 (1H, dd, J=7.88, 1.72 Hz), 7.42-7.44 (1H, d, J=8.4 Hz), 7.53-7.54 (1H, d, J=3.64 Hz), 8.01 (1H, d, J=1.64 Hz);
Mass (m/z): 407.5 (M+H)⁺.

Example 22

Preparation of 6-Chloro-1-[4'-methyl-3'-(1-methyl piperidin-4-yl oxy)benzenesulfonyl]-1H-indole Using a similar procedure as given in the Example 7 and 6-Chloro-1-(3-hydroxy-4-methyl)benzenesulfonyl-1H-indole (obtained from preparation 2), with some non-critical variations the above derivative was prepared.
IR (cm⁻¹): 2933, 1445, 1373, 1172;
¹H-NMR (ppm): 1.78-1.81 (2H, m), 1.92-1.94 (2H, m), 2.18 (3H, s), 2.31 (3H, s), 2.60 (2H, m), 2.73 (2H, m), 4.34 (1H, m), 6.61 (1H, d, J=3.6 Hz), 7.18-7.21 (2H, m), 7.23-7.24 (1H, d, J=1.64 Hz), 7.31-7.33 (1H, dd, J=7.84, 1.86 Hz), 7.42-7.44 (1H, d, J=8.36 Hz), 7.51-7.52 (1H, d, J=3.64 Hz), 8.02-8.03 (1H, d, J=1.64 Hz);
Mass (m/z): 419.5, 421.5 (M+H)⁺.

Example 23

Preparation of 1-[4'-Methyl-3'-(1-methyl piperidin-4-yl oxy)benzenesulfonyl]-1H-indole Using a similar procedure as given in the Example 7, with some non-critical variations the above derivative was prepared.
IR (cm⁻¹): 2933', 1445, 1372, 1170;
¹H-NMR (ppm): 1.73-1.76 (2H, m), 1.89-1.90 (2H, m), 2.16 (3H, s), 2.32 (5H, bs), 2.59 (2H, m), 4.27-4.31 (1H, m), 6.64-6.65 (1H, d, J=3.68 Hz), 7.15-7.33 (3H, m), 7.33-7.35 (2H, m), 7.51-7.53 (2H, m), 7.99-8.01 (1H, d, J=8.28 Hz);
Mass (m/z): 385.3 (M+H)⁺.

Example 24

Preparation of 5-Fluoro-1-(4'-methyl-3'-(1-methyl piperidin-4-yl oxy)benzenesulfonyl)-1H-indole hydrochloride Using a similar procedure as given in the Example 7, with some non-critical variations the above derivative was prepared.
IR (cm⁻¹): 2954, 2715, 1595, 1456, 1365, 1134;
¹H-NMR (ppm): 1.83-1.93 (2H, m), 2.04-2.08 (2H, m), 2.23 (3H, s), 2.51 (3H, s), 2.75 (2H, m), 3.02 (2H, m), 4.92 (1H, m), 6.82 (1 bs), 7.18-7.20 (1H, d, J=7.6 Hz), 7.39-7.40 (1H, d, J=6.5 Hz), 7.42-7.44 (1H, d, J=2.2 Hz), 7.47-7.50 (2H, m), 7.91-8.01 (2H, m), 10.67 (1H, bs);
Mass (m/z): 403.2 (M+H)⁻¹.

Example 25

Preparation of 4-Chloro-1-[4'-methyl-3'-(1-methyl piperidin-4-yl oxy)benzenesulfonyl]-1H-indole Using a similar procedure as given in the Example 7, with some non-critical variations the above derivative was prepared.
IR (cm⁻¹): 2933, 1445, 1373, 1172;
¹H-NMR (ppm): 1.73-1.78 (2H, m), 1.90-1.91 (2H, m), 2.18 (3H, s), 2.27-2.33 (2H, m), 2.39 (3H, s) 2.57 (2H, m), 4.29-4.32 (1H, m), 6.77-6.78 (1H, d, J=3.64 Hz), 7.17-7.19 (2H, m), 7.23-7.26 (2H, m), 7.33-7.35 (1H, dd, J=7.88, 1.80 Hz), 7.57-7.58 (1H, d, J=3.68 Hz), 7.90 (1H, m);
Mass (m/z): 419.5 (M+H)⁺.

Example 26

Preparation of 1-[4'-Ethyl-3'-(N,N-dimethylamino ethoxy)benzenesulfonyl]-1H-indole Using a similar procedure as given in the Example 1 and intermediate 1-(3-Hydroxy-4-ethyl)benzenesulfonyl indole (obtained from preparation 3), with some non-critical variations the above derivative was prepared.
IR (cm⁻¹): 2965, 2932, 1372, 1170, 1131;
¹H-NMR (ppm): 1.09-1.13 (3H, t, J=7.56 Hz), 2.33 (6H, s), 2.55-2.61 (2H, q, J=7.52 Hz), 2.71-2.74 (2H, t, J=5.76 Hz), 4.01-4.04 (2H, t, J=5.76 Hz), 6.64-6.65 (1H, d, J=3.56 Hz), 7.16-7.18 (1H, d, J=7.92 Hz), 7.22-7.31 (3H, m), 7.40-7.42 (1H, dd, J=7.96, 1.8 Hz), 7.52-7.54 (1H, d, =7.84 Hz), 7.55-7.56 (1H, d, J=3.64 Hz), 7.98-8.01 (1H, d, J=8.28 Hz);
Mass (m/z): 373.3 (M+H)⁺.

Example 27

Preparation of 5-Bromo-1-[4'-ethyl-3'-(N,N-dimethylamino ethoxy)benzenesulfonyl]-1H-indole Using a similar procedure as given in the Example 26, with some non-critical variations the above derivative was prepared.
IR (cm⁻¹): 2948, 1373, 1175;
¹H-NMR (ppm): 1.10-1.14 (31-1, t, J=7.5), 2.35 (6H, s), 2.57-2.62 (2H, q, J=7.5 Hz), 2.74-2.76 (2H, t, J=5.72 Hz), 4.03-4.06 (2H, t, J=5.73 Hz), 6.58-6.59 (1H, d, J=3.7 Hz), 7.17-7.19 (1H, d, J=7.95 Hz), 7.21-7.22 (1H, d, J=1.73 Hz), 7.38-7.41 (2H, m), 7.55-7.56 (1H, d, J=3.69 Hz), 7.66-7.67 (1H, d, J=1.84 Hz), 7.85-7.88 (1H, d, J=8.8 Hz);
Mass (m/z): 451, 453 (M+H)⁺.

Example 28

Preparation of 1-[4'-Ethyl-3'-(N,N-dimethylamino ethoxy)benzenesulfonyl]-5-methoxy-1H-indole Using a similar procedure as given in the Example 26, with some non-critical variations the above derivative was prepared.
IR (cm⁻¹): 2938, 1368, 1171;
¹H-NMR (cm⁻¹): 1.09-1.13 (3H, t, J=7.52 Hz), 2.33 (6H, s), 255-2.61 (2H, q, J=7.52 Hz), 2.71-2.74 (2H, t, J=5.76 Hz), 3.80 (3H, s), 4.01-4.04 (2H, t, J=5.76 Hz), 6.57-6.58 (1H, d, J=3.52 Hz), 6.90-6.93 (1H, dd, J=9.0, 2.48 Hz), 6.96-6.97 (1H, d, J=2.4 Hz); 7.15-7.17 (1H, d, J=7.96 Hz); 7.21 (1H, d, J=1.72 Hz); 7.36-7.39 (1H, dd, J=7.96, 1.76 Hz), 7.50-7.51 (1H, d, J=3.6 Hz), 7.87-7.89 (1H, d, J=8.96 Hz);
Mass (m/z): 403.3 (M+H)⁺.

Example 29

Preparation of 6-Chloro-1-[4'-Ethyl-3'-(N,N-dimethylamino ethoxy)benzenesulfonyl]-1H-indole Using a similar procedure as given in the Example 26, with some non-critical variations the above derivative was prepared.
IR (cm⁻¹): 2970, 2939, 1373, 1169;

¹H-NMR (ppm): 1.11-1.15 (3H, t, J=7.51 Hz), 2.33 (6H, s), 2.58-2.63 (2H, q, J=7.51), 2.73-2.76 (2H, t, J=5.69 Hz), 4.05-4.08 (2H, t, J=5.70 Hz), 6.61-6.62 (1H, d, J=3.69 Hz), 7.18-7.21 (2H, m), 7.25-7.26 (1H, d), 7.39-7.42 (1H, dd, J=7.92, 1.82 Hz), 7.42-7.44 (1H, d, J=8.40 Hz), 7.53-7.54 (1H, d, J=3.64 Hz), 8.02-8.03 (1H, d, J=1.72 Hz);
Mass (m/z): 407 (M+H)⁺.

Example 30

Preparation of 1-[4'-Ethyl-3'-(N,N-dimethylamino ethoxy)benzenesulfonyl]-5-fluoro-1H-indole Using a similar procedure as given in the Example 26, with some non-critical variations the above derivative was prepared.
IR (cm⁻¹): 2934, 1374, 1171;
¹H-NMR (ppm): 1.10-1.14 (3H, t, J=7.51 Hz), 2.34 (6H, s), 2.56-2.62 (2H, q), 2.72-2.75 (2H, t, J=5.76 Hz), 4.02-4.05 (2H, t, J=5.76 Hz), 6.60-6.61 (1H, d, J=3.44 Hz), 7.03-7.04 (1H, m), 7.16-7.22 (3H, m), 7.38-7.40 (1H, dd, J=7.88, 1.80 Hz), 7.58-7.59 (1H, d, J=3.64 Hz), 7.91-7.93 (1H, q, J=4.64 Hz);
Mass (m/z): 391 (M+H)⁺.

Example 31

Preparation of 1-[4'-Ethyl-3'-(N,N-dimethylamino propoxy)benzenesulfonyl]-1H-indole Using a similar procedure as given in the Example 4 and (3-Hydroxy-4-ethyl benzenesulfonyl) indole (obtained from preparation 3), with some non-critical variations the above derivative was prepared.
IR (cm⁻¹): 2947, 1373, 1171, 1137;
¹H-NMR (ppm): 1.09-1.13 (3H, t, J=7.48 Hz), 1.91-1.98 (2H, m), 2.26 (6H, s), 2.43-2.46 (2H, t, J=7.44 Hz), 2.55-2.60 (2H, q, J=7.52 Hz), 3.96-3.99 (2H, t, J=6.2 Hz), 6.65 (1H, d, J=3.84 Hz), 7.15-7.17 (1H, d, J=7.92 Hz), 7.22-7.31 (3H, m), 7.38-7.40 (1H, dd, J 7.92, 1.76 Hz), 7.52-7.54 (1H, d, J=7.8 Hz), 7.55-7.56 (1H, d, J=3.68 Hz), 7.99-8.01 (1H, d, J=8.48 Hz);
Mass (m/z): 387.4 (M+H)⁺.

Example 32

Preparation of 5-Bromo-1-[4'-Ethyl-3'-(N,N-dimethylamino propoxy)benzenesulfonyl]-1H-indole Using a similar procedure as given in the Example 31, with some non-critical variations the above derivative was prepared.
IR (cm⁻¹): 2948, 1373, 1175;
¹H-NMR (ppm): 1.10-1.14 (3H, t, J=7.52), 1.96-2.02 (2H, m), 2.29 (6H, s), 2.48-2.52 (2H, t, J=7.12 Hz), 2.56-2.61 (2H, q, J=7.52 Hz), 3.97-4.0 (2H, t, J=6.2 Hz), 6.58-6.59 (1H, d, J=3.94 Hz), 7.16-7.18 (1H, d, J=7.95 Hz), 7.21-7.22 (1H, d, J=1.76 Hz), 7.36-7.41 (2H, m), 7.55-7.56 (1H, d, J=3.63 Hz), 7.66-7.67 (1H, d, J=1.85 Hz), 7.86-7.88 (1H, d, J=8.79 Hz);
Mass (m/z): 465, 467 (M+H)⁺.

Example 33

Preparation of 1-[4'-Ethyl-3'-(N,N-dimethylamino propoxy)benzenesulfonyl]-6-chloro-1H-indole Using a similar procedure as given in the Example 31, with some non-critical variations the above derivative was prepared.
IR (cm⁻¹): 2939, 1374, 1169;
¹H-NMR (ppm): 1.11-1.15 (31-1, t, J=7.51), 1.92-1.99 (2H, m), 2.25 (6H, s), 2.41-2.46 (2H, t), 2.57-2.62 (2H, q), 3.99-4.02 (2H, t), 6.61-6.62 (1H, d, J=3.59 Hz), 7.18-7.21 (2H, m), 7.27 (1H, d, J=1.78 Hz), 7.37-7.39 (1H, dd, J=1.81 Hz and 7.91 Hz), 7.42-7.44 (1H, d, J=8.40 Hz), 7.53-7.54 (1H, d, J=3.66 Hz), 8.03 (1H, d, J=1.57 Hz);
Mass (m/z): 421 (M+H)⁺.

Example 34

Preparation of 1-[4'-Ethyl-3'-(N,N-dimethylamino propoxy)benzenesulfonyl]-5-methoxy-1H-indole Using a similar procedure as given in the Example 31, with some non-critical variations the above derivative was prepared.
IR (cm⁻¹): 2940, 1370, 1172;
¹H-NMR (ppm): 1.09-1.13 (3H, t, J=7.51 Hz), 1.91-1.99 (2H, m), 2.25 (6H, s); 2.42-2.45 (2H, t, J=7.32 Hz), 2.55-2.60 (2H, q, J=7.48 Hz), 3.81 (3H, s), 3.96-3.99 (2H, t, J=6.16 Hz), 6.57-6.58 (1H, d, J=3.55 Hz), 6.90-6.93 (1H, dd, J=8.99, 2.38 Hz), 6.97 (1H, d, J=2.2 Hz), 7.14-7.16 (1H, d, J=7.92 Hz), 7.22 (1H, d, J=1.41 Hz), 7.34-7.36 (1H, dd, J=7.86, 1.54 Hz), 7.50-7.51 (1H, d, J=3.57 Hz), 7.87-7.89 (1H, d, J=8.95 Hz);
Mass (m/z): 417.6 (M+H)⁺.

Example 35

Preparation of 1-[4'-Ethyl-3'-(N,N-dimethylamino propoxy)benzenesulfonyl]-5-fluoro-1H-indole Using a similar procedure as given in the Example 31, with some non-critical variations the above derivative was prepared.
IR (cm⁻¹): 2934, 1374, 1171;
¹H-NMR (ppm): 1.10-1.14 (3H, t, J=7.51 Hz), 1.92-1.99 (2H, m), 2.26 (6H, s), 2.44-2.47 (2H, t), 2.47-2.61 (2H, q), 3.97-4.00 (2H, t), 6.60-6.61 (1H, d, J=4.2 Hz), 7.03-7.04 (1H, m), 7.16-7.23 (3H, m), 7.35-7.38 (1H, dd, J=7.88, 1.84 Hz), 7.58-7.59 (1H, d, J=3.63 Hz), 7.91-7.93 (1H, d, J=9.0 Hz);
Mass (m/z): 405 (M+H)⁺.

Example 36

Preparation of 1-[4'-Isopropyl-3'-(N,N-dimethylamino ethoxy)benzenesulfonyl]-1H-indole Using a similar procedure as given in the Example 31, with some non-critical variations the above derivative was prepared.
IR (cm⁻¹): 2962, 1372, 1173;
¹H-NMR (ppm): 1.11-1.13 (6H, d, J=6.91 Hz), 2.35 (6H, s), 2.75-2.78 (2H, t, J=5.76 Hz), 3.22-3.29 (1H, septet), 4.03-4.06 (2H, t, J=5.79 Hz), 6.64-6.65 (1H, d, J=3.59 Hz), 7.21-7.25 (3H, m), 7.29-7.33 (1H, m), 7.43-7.45 (1H, dd, J=8.05, 1.80 Hz), 7.53-7.55 (1H, d, J=7.82 Hz), 7.56 (1H, d, J=3.69 Hz), 8.00-8.02 (1H, d, J=8.8 Hz);
Mass (m/z): 387.4 (m+H)⁺.

Example 37

Preparation of 1-[4'-Isopropyl-3'-(N,N-dimethylamino ethoxy)benzenesulfonyl]-5-methoxy-3-methyl-1H-indole Using a similar procedure as given in the Example 1, with some non-critical variations the above derivative was prepared.
IR (cm⁻¹): 2960, 1365, 1172;

¹H-NMR (ppm): 1.06-1.08 (6H, d, J=6.90 Hz), 2.16 (3H, d), 2.18 (6H, s), 2.57-2.60 (2H, t), 3.14-3.19 (1H, septet), 3.75 (3H, s), 4.05-4.07 (2H, t), 6.91-6.94 (1H, dd, J=8.97, 2.5 Hz), 7.00-7.01 (1H, d, J=2.45 Hz), 7.32-7.35 (2H, m), 7.39-7.41 (1H, dd, J=8.07, 1.74 Hz), 7.54 (1H, d, J=1.15 Hz), 7.82-7.84 (1H, d, J=8.94 Hz);
Mass (m/z): 431.4 (M+H)⁺.

Example 38

Preparation of 1-[4'-Isopropyl-3'-(1-dimethylamino-2-Propoxy)benzenesulfonyl]-1H-indole Using a similar procedure as given in the Example 1, with some non-critical variations the above derivative was prepared.
IR (cm⁻¹): 2966, 1371, 1172;
¹H-NMR (ppm): 1.10-1.12 (6H, d), 1.20-1.22 (3H, d, J=6.12 Hz), 2.28 (6H, s), 2.41-2.46 (1H, dd), 2.56-2.61 (1H, dd), 3.20-3.27 (1H, m), 4.44-4.48 (1H, m), 6.65-6.66 (1H, d, J=3.60 Hz), 7.20-7.24 (2H, m), 7.29-7.33 (2H, m), 7.39-7.41 (1H, dd, J=8.08, 1.8 Hz), 7.52-7.55 (2H, m), 8.01-8.03 (1H, m);
Mass (m/z): 401.3 (M+H)⁺.

Example 39

Preparation of 1-[4'-Isopropyl-3'-(2-dimethylamino-1-propoxy)benzenesulfonyl]-1H-indole Using a similar procedure as given in the Example 1, with some non-critical variations the above derivative was prepared.
IR (cm⁻¹): 2960, 1369, 1172, 1130;
¹H-NMR (ppm): 1.12-1.16 (9H, m), 2.35 (6H, s), 2.95-2.99 (1H, m), 3.24-3.27 (1H, m), 3.77-3.81 (1H, m), 3.99-4.02 (1H, m), 6.65-6.66 (1H, m), 7.22-7.25 (3H, m), 7.32 (1H, m), 7.42-7.44 (1H, m), 7.53-7.55 (1H, d, J=7.76 Hz), 7.56-7.57 (1H, d, J=3.64 Hz), 8.00-8.02 (1H, dd, J=8.2 Hz);
Mass (m/z): 401.3 (M+H)⁺.

Example 40

Preparation of 1-[4'-Isopropyl-3'-(N,N-dimethylamino ethoxy)benzenesulfonyl]-3-methyl-1H-indole Using a similar procedure as given in the Example 1, with some non-critical variations the above derivative was prepared.
IR (cm⁻¹): 2965, 1369, 1215, 1172;
¹H-NMR (ppm): 1.11-1.13 (6H, d, J=6.92 Hz), 2.24 (3H, s), 2.34 (6H, s), 2.74 (2H, t), 3.23-3.26 (1H, m), 4.02-4.05 (2H, t), 7.20-7.34 (5H, m), 7.40-7.42 (1H, dd, J=8.05, 1.84 Hz), 7.45-7.47 (1H, d, J=8.18 Hz), 7.98-8.00 (1H, d, J=8.23 Hz);
Mass (m/z): 401.3 (M+H)⁺.

Example 41

Preparation of 1-[4'-Isopropyl-3'-(N,N-dimethylamino propoxy)benzenesulfonyl]-3-methyl-1H-indole Using a similar procedure as given in the Example 1, with some non-critical variations the above derivative was prepared.
IR (cm⁻¹): 2960, 1369, 1174;
¹H-NMR (ppm): 1.12-1.13 (6H, d, J=6.92), 1.94-1.98 (2H, m), 2.17-2.27 (9H, s), 2.44-2.48 (2H, t), 3.21-3.25 (1H, m), 3.96-3.99 (2H, t), 7.18-7.20 (1H, d, J=8.08 Hz), 7.22-7.33 (4H, m), 7.37-7.40 (1H, dd, J=8.08, 1.88 Hz), 7.45-7.47 (1H, d, J=7.84), 7.99-8.01 (1H, d; J=8.24 Hz);
Mass (m/z): 415 (M+H)⁺.

Example 42

Preparation of 1-[4'-Isopropyl-3'-(N,N-dimethylamino ethoxy)benzenesulfonyl]-5-methoxy-1H-indole Using a similar procedure as given in the Example 1, with some non-critical variations the above derivative was prepared.
IR (cm⁻¹): 2956, 1477, 1357, 1234;
¹H-NMR (ppm): 1.11-1.13 (6H, d), 2.34 (6H, s), 2.72-2.75 (2H, t), 3.22-3.28 (1H, septet), 3.81 (3H, s), 4.01-4.04 (2H, t), 6.58-6.59 (1H, d, J=3.60 Hz), 6.91-6.94 (1H, dd, J=2.48 Hz), 6.97-6.98 (1H, d, J=3.80 Hz), 7.20-7.22 (2H, m), 7.39-7.42 (1H, dd, J=8.08, 1.84 Hz), 7.51 (1H, d, J=3.6 Hz), 7.88-7.90 (1H, d, J=8.96 Hz);
Mass (m/z): 417.5 (M+H)⁺.

Example 43

Preparation of 1-[4'-Isopropyl-3'-(N,N-dimethylamino propoxy)benzenesulfonyl]-5-Methoxy-1H-indole Using a similar procedure as given in the Example 1, with some non-critical variations the above derivative was prepared.
IR (cm⁻¹): 2960, 1365, 1174, 1147;
¹H-NMR (ppm): 1.12-1.14 (6H, d), 1.92-1.99 (2H, m), 2.26 (6H, s), 2.43-2.47 (2H, t), 3.22-3.27 (1H, m), 3.81 (3H, s), 3.96-3.99 (2H, t), 6.57-6.58 (1H, m, J=3.65 Hz), 6.92-6.94 (1H, dd, J=8.96, 2.44 Hz), 6.97-6.98 (1H, d, J=2.44 Hz), 7.19-7.21 (1H, d, J=8.08 Hz), 7.23 (1H, d, J=1.84 Hz), 7.37-7.39 (1H, dd, J=8.08, 1.84 Hz), 7.51-7.52 (1H, d, J=3.60 Hz), 7.88-7.90 (1H, d, J=9.0 Hz);
Mass (m/z): 431.3 (M+H)⁺.

Example 44

Preparation of 1-[4'-Isopropyl-3'-(2-dimethylamino propoxy) benzenesulfonyl]-5-Methoxy-1H-indole Using a similar procedure as given in the Example 1, with some non-critical variations the above derivative was prepared.
IR (cm⁻¹): 2960, 1365, 1143;
¹H-NMR (ppm): 1.12-1.14 (6H, d), 1.17-1.19 (3H, d), 2.38 (6H, s), 3.02-3.06 (1H, m), 3.23-3.26 (1H, m), 3.81 (3H, s), 3.82-3.84 (1H, m), 3.99-4.03 (1H, m), 6.58-6.59 (1H, m), 6.91-6.94 (1H, dd, J=9.00, 2.52 Hz), 6.98 (1H, d, J=2.40 Hz), 7.21-7.23 (2H, m, J=7.64, 2.16-Hz), 7.39-7.42 (1H, dd, J=8.04, 1.76 Hz), 7.51-7.52 (1H, d, J=3.64 Hz), 7.89-7.91 (1H, d, J=9.0 Hz);
Mass (m/z): 431.3 (M+H)⁺.

Example 45

Preparation of 1-[4'-Isopropyl-3'-(1-dimethylamino-2-propoxy)benzenesulfonyl]-5-methoxy-1H-indole Using a similar procedure as given in the Example 1, with some non-critical variations the above derivative was prepared.
IR (cm⁻¹): 2950, 1369, 1172, 1145;

¹H-NMR (ppm): 1.10-1.12 (6H, m), 1.21-1.22 (3H, d, J=6.12 Hz), 2.28 (6H, s), 2.40-2.45 (1H, m), 2.55-2.60 (1H, m), 3.20-3.25 (1H, m), 3.81 (3H, s), 4.43-4.47 (1H, m), 6.57-6.58, (1H, d, J=3.6 Hz), 6.90-6.93 (1H, dd, 9.0, 2.52 Hz), 6.97-6.98 (1H, d, J=2.44 Hz), 7.19-7.21 (1H, d, J=8.12 Hz), 7.29 (1H, d, J=1.76 Hz), 7.35-7.37 (1H, dd, 8.08, 1.84 Hz), 7.49-7.50 (1H, d, J=3.6 Hz), 7.89-7.91 (1H, d, J=9.0 Hz);
Mass (m/z): 430.9 (M+H)⁺.

Example 46

Preparation of 1-[4'-Isopropyl-3'-(N,N-dimethylamino ethoxy)benzenesulfonyl]-5-fluoro-1H-indole Using a similar procedure as given in the Example 1, with some non-critical variations the above derivative was prepared.
IR (cm⁻¹): 2950, 1362, 1201, 1180;
¹H-NMR (ppm): 1.12-1.14 (6H, d, J=6.92 Hz), 2.35 (6H, s), 2.75-2.78 (2H, t, J=5.76 Hz), 3.24-3.28 (1H, m), 4.03-4.06 (2H, t, J=5.76), 6.61-6.62 (1H, d, J=3.72 Hz), 6.92-7.04 (1H, m), 7.17-7.19 (1H, m), 7.22-7.25 (2H, m), 7.40-7.42 (1H, dd, J=8.08, 1.84 Hz), 7.58-7.59 (1H, d, J=3.68 Hz), 7.92-7.93 (1H, m, J=4.4 Hz);
Mass (m/z): 405.4 (M+H)⁺.

Example 47

Preparation of 1-[4'-Isopropyl-3'-(N,N-dimethylamino propoxy)benzenesulfonyl]-5-fluoro-1H-indole Using a similar procedure as given in the Example 1, with some non-critical variations the above derivative was prepared.
IR (cm⁻¹): 2964, 1371, 1217, 1174;
¹H-NMR (ppm): 1.13-1.14 (6H, d, J=6.88 Hz), 1.92-1.99 (2H, m), 2.25 (6H, s), 2.43-2.46 (2H, t, J=7.12 Hz), 3.21-3.28 (1H, septet), 3.97-4.00 (2H, t, J=6.2 Hz), 6.61-6.62 (1H, d, J=3.68 Hz), 7.04 (1H, m), 7.17-7.23 (3H, m), 7.37-7.40 (1H, dd, J=8.0, 1.80 Hz), 7.58-7.59 (1H, d, J=3.68 Hz), 7.92-7.96 (1H, dd, J=9.08, 4.4 Hz);
Mass (m/z): 419.4 (M+H)⁺.

Example 48

1-[4'-Isopropyl-3'-(2-dimethylamino propoxy)benzenesulfonyl]-5-fluoro-1H-indole

Using a similar procedure as given in the Example 1, with some non-critical variations the above derivative was prepared.
IR (cm⁻¹): 2964, 1462, 1373, 1174;
¹H-NMR (ppm): 1.12-1.15 (6H, m), 1.19-1.21 (31-1, d), 2.40 (6H, s), 3.11-3.15 (1H, m), 3.24-3.27 (1H, m), 3.84-3.88 (1H, m), 4.02-4.05 (1H, m), 6.61-6.62 (1H, d, J=3.72 Hz), 7.04-7.05 (1H, m), 7.17-7.20 (1H, m), 7.22-7.23 (2H, m), 7.41-7.43 (1H, dd, J=8.08, 1.8 Hz), 7.59-7.60 (1H, d, J=3.64 Hz), 7.94-8.05 (1H, d, J=4.04 Hz);
Mass (m/z): 419.4 (M+H)⁺.

Example 49

Preparation of 1-[4'-Isopropyl-3'-(1-dimethyl amino-2-propoxy)benzenesulfonyl]-5-fluoro-1H-indole Using a similar procedure as given in the Example 1, with some non-critical variations the above derivative was prepared.
IR (cm⁻¹): 2968, 1373, 1247, 1182;
¹H-NMR (ppm): 1.10-1.13 (6H, m), 1.21-1.24 (3H, d), 2.28 (6H, s), 2.41-2.45 (1H, m), 2.56-2.61 (1H, m), 3.22-3.26 (1H, m), 4.43-4.48 (1H, m), 6.60-6.61 (1H, d, J=3.56 Hz), 7.03 (1H, d, J=1.8 Hz), 7.17-7.19 (1H, dd, J=8.76, 2.52 Hz), 7.21-7.23 (1H, d, J=8.12 Hz), 7.30 (1H, d, J=1.8 Hz), 7.36-7.38 (1H, d, J=8.08 Hz), 7.57-7.58 (1H, d, J=3.68 Hz), 7.93-7.94 (1H, dd, J=4.40 Hz);
Mass (m/z): 419.4 (M+H)⁺.

Example 50

Preparation of 1-[4'-Isopropyl-3'-(N,N-dimethylamino ethoxy)benzenesulfonyl]-5-fluoro-3-methyl-1H-indole Using a similar procedure as given in the Example 1, with some non-critical variations the above derivative was prepared.
IR (cm⁻¹): 2929, 2962, 1369, 1176;
¹H-NMR (ppm): 1.12-1.14 (6H, d, J=6.92 Hz), 2.20 (3H, s), 2.34 (6H, s), 2.72-2.75 (2H, t, J=5.8 Hz), 3.22-3.29 (1H, m), 4.02-4.05 (2H, t, J=5.84 Hz), 7.04-7.10 (2H, m), 7.21-7.23 (2H, m), 7.32 (1H, d, J=0.96 Hz), 7.37-7.39 (1H, dd, J=8.08, 1.8 Hz), 7.91-7.94 (1H, m);
Mass (m/z): 419.4 (M+H)⁺.

Example 51

Preparation of 1-[4'-Isopropyl-3'-(N,N-dimethylamino propoxy)benzenesulfonyl]-5-fluoro-3-methyl-1H-indole Using a similar procedure as given in the Example 1, with some non-critical variations the above derivative was prepared.
IR (cm⁻¹): 2962, 1367, 1247, 1178;
¹H-NMR (ppm): 1.12-1.14 (6H, d, J=6.92 Hz), 1.96-2.04 (2H, m), 2.20 (3H, s), 2.31 (6H, s), 2.52-2.55 (2H, t, J=7.6 Hz), 3.19-3.25 (1H, m), 3.95-3.98 (2H, t, J=6.16 Hz), 7.03-7.10 (2H, m), 7.19-7.21 (2H, m), 732-7.36 (2H, m), 7.91-7.94 (1H, m);
Mass (m/z): 433.4 (M+H)⁺.

Example 52

Preparation of 5-Methoxy-1-[4'-isopropyl-3'-(1-methyl piperidin-4-yl oxy)benzenesulfonyl]-1H-indole Using a similar procedure as given in the Example 7, with some non-critical variations the above derivative was prepared.
IR (cm⁻¹): 2966, 1614, 1467, 1361, 1139;
¹H-NMR (ppm): 1.12-1.13 (6H, d, J=6.84 Hz), 1.76-1.90 (2H, m), 1.96-2.04 (2H, m), 2.31 (5H, bs), 2.60 (2H, m), 3.20-3.26 (1H, m), 3.81 (3H, s), 4.29 (1H, m), 6.57-6.58 (1H, d, J=3.48 Hz), 6.90-6.93 (1H, dd, J=2.17, 8.98 Hz), 6.97 (1H, d, J=2.08 Hz), 7.15 (1H, s), 7.20-7.22 (1H, d, J=8.09 Hz), 7.35-7.37 (1H, dd, J=−7.99 Hz), 7.48-7.49 (1H, d, J=3.53 Hz), 7.89-7.91 (1H, d, J=8.97 Hz);
Mass (m/z): 443.5 (M+H)⁺.

Example 53

Preparation of 5-Fluoro-1-[4'-isopropyl-3'-(1-methyl piperidin-4-yl oxy)benzenesulfonyl]-1H-indole Using a similar procedure as given in the Example 7, with some non-critical variations the above derivative was prepared.

Melting Range: 73.2-74.5° C.

IR (cm$^{-1}$): 3018, 2964, 1591, 1462, 1348, 1141;

$^1$H-NMR (ppm): 1.13-1.15 (6H, d, J=6.89 Hz), 1.77-1.80 (2H, m), 1.89-1.91 (2H, m), 2.31 (5H, bs), 2.59 (2H, m), 3.22-3.28 (1H, m), 4.30 (1H, m), 6.61-6.62 (1H, d, J=3.60 Hz), 7.01-7.06 (1H, dt, J=9.0, 2.48 Hz), 7.16 (1H, d, J=1.44 Hz), 7.17-7.20 (1H, dd, J=8.79, 2.4 Hz), 7.23-7.25 (1H, d, J=8.13 Hz), 7.36-7.38 (1H, dd, J=8.08, 1.5 Hz), 7.57 (1H, d, J=3.64 Hz), 7.94-7.97 (1H, m);

Mass (m/z): 431.4 (M+H)$^+$.

Example 54

Preparation of 3-Methyl-1-[4'-methyl-3'-(1-methyl piperidin-4-yl oxy)benzenesulfonyl]-1H-indole Using a similar procedure as given in the Example 7, with some non-critical variations the above derivative was prepared.

IR (cm$^{-1}$): 2931, 2794, 1593, 1450, 1365, 1168;

$^1$H-NMR (ppm): 1.61-1.64 (2H, m), 1.83-1.84 (2H, m), 2.15 (3H, s), 2.21 (3H, s), 2.24 (3H, s), 2.54 (2H, m), 2.89 (2H, m), 4.47 (1H, m), 7.24-7.28 (1H, m), 7.29 (1H, s), 7.31-7.32 (1H, d, J=1.69 Hz), 7.33-7.35 (1H, dd, J=8.34, 1.18 Hz), 7.37-7.41 (1H, dt, J=6.25, 1.13 Hz), 7.46 (1H, d, J=1.2 Hz), 7.51-7.53 (1H, d, J=7.8 Hz), 8.01-8.03 (1H, d, J=8.24 Hz);

Mass (m/z): 399.2 (M+H)$^+$.

Example 55

Preparation of 5-Methoxy-1-[4-ethyl-3-(1-methyl piperidin-4-yl oxy)benzenesulfonyl]-1H-indole Using a similar procedure as given in the Example 7, with some non-critical variations the above derivative was prepared.

IR (cm$^{-1}$): 2958, 11467, 1369, 1143, 1037;

$^1$H-NMR (ppm): 1.10-1.43 (3H, t, J=7.28 Hz), 1.78 (2H, m), 1.91-1.92 (2H, m), 2.33 (3H, s), 2.41-2.42 (2H, m), 2.55-2.58 (2H, q), 2.60 (2H, m), 3.81 (3H, s), 4.32 (1H, m), 6.57-6.58 (1H, d, J=3.5 Hz), 6.90-6.93 (1H, dd, J=8.9, 2.4 Hz), 6.97 (1H, d, J=2.3 Hz), 7.14 (1H, d, J=1.2 Hz), 7.16-7.18 (1H, d, J=7.9 Hz), 7.34-7.36 (1H, dd, J=7.8, 1.4 Hz), 7.48-7.49 (1H, d, J=3.5 Hz), 7.88-7.90 (1H, d, J=8.9 Hz);

Mass (m/z): 429.3 (M+H)$^+$.

Example 56

Preparation of 5-Methoxy-1-[4'-methoxy-3'-(piperidin-4-yl oxy)benzenesulfonyl]-1H-indole hydrochloride Using a similar procedure as given in the Example 7, with some non-critical variations the above derivative was prepared.

Melting Range: 231.2-232.7° C.

IR (cm$^{-1}$): 2978, 2927, 1615, 1435, 1371, 1143, 1030;

$^1$H-NMR (ppm): 1.69 (2H, m), 1.89-1.91 (2H, m), 3.04 (2H, m), 3.17 (2H, m), 3.73 (3H, s), 3.77 (3H, s), 4.63 (1H, m), 6.71-6.72 (1H, d, J=3.4 Hz), 6.89-6.92 (1H, dd, J=8.96, 2.12 Hz), 7.09-7.08 (1H, d, J=2.02 Hz), 7.13-7.11 (1H, d, J=8.7 Hz), 7.49 (1H, s), 7.55-7.53 (1H, dd, J=8.62 Hz), 7.74-7.73 (1H, d, J=3.46 Hz), 7.84-7.86 (1H, d, J=8.97 Hz), 8.86 (1H, bs);

Mass (m/z): 417.4 (M+H)$^+$.

Example 57

Preparation of 5-Methoxy-1-[4'-methoxy-3'-(1-methyl piperidin-4-34 oxy)benzenesulfonyl]-1H-indole Using a similar procedure as given in the Example 7, with some non-critical variations the above derivative was prepared.

IR (cm$^{-1}$): 2942, 2797, 1615, 1466, 1367, 1143, 1030;

$^1$H-NMR (ppm): 1.73-1.78 (2H, m), 1.84-1.85 (2H, m), 2.02-2.04 (2H, m), 2.30 (3H, s), 2.68-2.69 (2H, m), 3.80 (3H, s), 3.82 (3H, s), 4.14 (1H, m), 6.56-6.57 (1H, d, J=3.56 Hz), 6.81-6.83 (1H, d, J=8.62 Hz), 6.89-6.92 (1H, dd, J=8.98, 2.40 Hz), 6.95-6.96 (1H, d, J=2.32 Hz), 7.22-7.23 (1H, d, J=2.1 Hz), 7.45-7.47 (2H, m), 7.87-7.89 (1H, d, J=8.97 Hz);

Mass (m/z): 431.3, (M+H)$^+$.

Example 58

Preparation of 5-Fluoro-1-[4'-methoxy-3'-(1-methyl piperidin-4-yl oxy)benzenesulfonyl]-1H-indole Using a similar procedure as given in the Example 7, with some non-critical variations the above derivative was prepared.

IR (cm$^{-1}$): 2934, 2778, 1614, 1462, 1365, 1142, 1082;

$^1$H-NMR (ppm): 1.71-1.78 (2H, m), 1.85 (2H, m), 2.04 (2H, m), 2.30 (3H, s), 2.69 (2H, m), 3.83 (3H, s), 4.14 (1H, m), 6.59-6.60 (1H, d, J=3.45 Hz), 6.83-6.85 (1H, d, J=8.62 Hz), 7.0-7.05 (1H, dt, J=9.0, 2.16 Hz), 7.15-7.18 (1H, dd, J=86.7, 2.16 Hz), 7.23-7.24 (1H, d, J=1.76 Hz), 7.46-7.49 (1H, dd, J=8.56, 1.84 Hz), 7.55-7.56 (1H, d, J=3.49 Hz), 7.91-7.95 (1H, q, J=8.96, 4.32 Hz);

Mass (m/z): 419.3 (M+H)$^+$.

Example 59

Preparation of 5-Fluoro-1-[4'-chloro-3'-(1-methyl piperidin-4-yl oxy)benzenesulfonyl]-1H-indole Using a similar procedure as given in the Example 7, with some non-critical variations the above derivative was prepared.

IR (cm$^{-1}$): 2950, 1463, 1366, 1176, 1046;

$^1$H-NMR (ppm): 1.77-1.83 (2H, m), 1.88-1.93 (2H, m), 2.31 (3H, s), 2.35 (2H, m), 2.61 (2H, m), 4.14 (1H, m), 6.64 (1H, d, 3.55 Hz), 7.02-7.07 (1H, dt, J=9.0, 2.51 Hz), 7.18-7.20 (1H, dd, J=8.63, 2.49 Hz), 7.27-7.28 (1H, d, J=1.99 Hz), 7.33-7.35 (1H, dd, J=8.34, 2.03 Hz), 7.40-7.42 (1H, d, J=8.34 Hz), 7.52-7.54 (1H, d, J=3.65 Hz), 7.91-7.94 (1H, q, J=9.04, 4.38 Hz);

Mass (m/z): 423.26, (M+H)$^+$.

Example 60

Preparation of 5-Fluoro-3-methyl-1-[4'-methoxy-3'-(1-methyl piperidin-4-yl oxy)benzenesulfonyl]-1H-indole Using a similar procedure as given in the Example 7, with some non-critical variations the above derivative was prepared.

IR (cm$^{-1}$): 2939, 1369, 1167, 1088;

$^1$H-NMR (ppm): 1.85-1.86 (2H, m), 1.89-1.90 (2H, m), 2.19 (3H, s), 2.21-2.24 (2H, m), 2.31 (3H, s), 2.70 (2H, m), 3.82 (3H, s), 4.18 (1H, m), 6.82-6.84 (1H, d, J=8.6 Hz), 7.0-7.05 (1H, dt, J=8.90, 2.4 Hz), 7.07-7.10 (1H, dd, J=8.63, 2.40 Hz), 7.21-7.22 (1H, d, J=2.1 Hz), 7.29 (1H, s), 7.44-7.46 (1H, dd, J=8.5, 2.1 Hz), 7.91-7.94 (1H, q, J=8.9, 4.3 Hz);
Mass (m/z): 433.4, (M+14)$^+$.

Example 61

Preparation of 5-Methoxy-3-methyl-1-[4'-isopropyl-3'-(1-methyl piperidin-4-yl oxy)benzenesulfonyl]-1H-indole Using a similar procedure as given in the Example 7, with some non-critical variations the above derivative was prepared.
Melting Range: 73.2-74.5° C.
IR (cm$^{-1}$): 3113, 2941, 1595, 1475, 1365, 1172;
$^1$H-NMR (ppm): 1.12-1.14 (61-1, d, J=6.87 Hz), 1.77-1.91 (4H, m), 2.20 (3H, s), 2.32 (5H, bs), 2.61 (2H, m), 3.19-3.26 (1H, m), 3.83 (3H, s); 4.29 (1H, m), 6.87 (1H, d, J=1.98 Hz), 6.90-6.93 (1H, dd, J=8.90, 2.23 Hz), 7.13 (1H, s), 7.19-7.21 (1H, d, J=8.08 Hz), 7.24 (1H, s), 7.33-7.35 (1H, dd, J=8.08 Hz), 7.88-7.90 (1H, d, J=8.92 Hz);
Mass (m/z): 457.3 (M+H)$^+$.

Example 62

Preparation of 6-Chloro-1-[4'-methoxy-3'-(1-methyl piperidin-4-yl oxy)benzenesulfonyl]-1H-indole Using a similar procedure as given in the Example 7, with some non-critical variations the above derivative was prepared.
Melting Range: 112-115° C.
IR (cm$^{-1}$): 2966, 2786, 1581, 1459, 1374, 1140, 1092;
$^1$H-NMR (ppm): 1.74-1.77 (2H, m), 1.78-1.81 (2H, m), 2.25 (2H, m), 2.31 (3H, s), 2.70 (2H, m), 3.84 (3H, s), 4.22 (1H, m), 6.60-6.61 (1H, d, J=3.44 Hz), 6.85-6.87 (1H, d, J=8.62 Hz), 7.19-7.21 (1H, dd, J=8.25 Hz), 7.30 (1H, d, J=1.72 Hz), 7.42-7.45 (1H, d, J=8.37 Hz), 7.47-7.52 (2H, m), 8.02 (1H, s);
Mass (m/z): 435.3 (M+H)$^+$.

Example 63

Preparation of 5-Bromo-1-[4'-methoxy-3'-(1-methyl piperidin-4-yl oxy)benzenesulfonyl]-1H-indole Using a similar procedure as given in the Example 7, with some non-critical variations the above derivative was prepared.
Melting Range: 127.2-128° C.
IR (cm$^{-1}$): 2933, 2806, 1585, 1440, 1369, 1170, 1092;
$^1$H-NMR (ppm): 1.71-1.78 (2H, m), 1.84 (2H, m), 2.17-2.18 (2H, m), 2.30 (3H, s), 2.69 (2H, m), 3.83 (3H, s), 4.15 (1H, m), 6.57-6.58 (1H, d, J=3.48 Hz), 6.83-6.85 (1H, d, J=8.62 Hz), 7.22 (1H, d, J=1.87 Hz), 7.38-7.40 (1H, dd, J=8.77, 1.25 Hz), 7.46-7.49 (1H, dd, J=8.59, 1.92 Hz), 7.51-7.52 (1H, d, J=3.49 Hz), 7.65-7.66 (1H, d, J=1.11 Hz), 7.86-7.88 (1H, d, J=8.78 Hz);
Mass (m/z): 479.2 (M+H)$^+$.

Example 64

Preparation of 3-Bromo-5-fluoro-1-[4'-methoxy-3'-(1-methyl piperidin-4-yl oxy)benzenesulfonyl]-1H-indole Using a similar procedure as given in the Example 7, with some non-critical variations the above derivative was prepared.

IR (cm$^{-1}$): 2942, 2795, 1619, 1468, 1370, 1139, 1031;
$^1$H-NMR (ppm): 1.88-1.97 (4H, m), 2.17 (2H, m), 2.29 (3H, s), 2.76-2.79 (2H, m), 3.90 (3H, s), 4.24 (1H, m), 6.59-6.60 (1H, d, J=3.65 Hz), 6.91 (1H, d, J=2.46 Hz), 6.93-6.96 (1H, d, J=8.96 Hz), 7.20-7.22 (1H, dd, J=8.78, 2.44 Hz), 7.52-7.56 (1H, q, J=9.01, 4.32 Hz), 7.77-7.78 (1H, d, J=3.67 Hz), 7.92-7.95 (1H, d, J=8.95 Hz);
Mass (m/z): 497.55 (M+H)$^+$.

Example 65

Preparation of 3-Bromo-5-fluoro-1-[4'-ethyl-3'-(piperidin-4-yl oxy)benzenesulfonyl]-1H-indole hydrochloride Using a similar procedure as given in the Example 7, with some non-critical variations the above derivative was prepared.
Melting Range: 289.9-291.5° C.
IR (cm$^{-1}$): 2965, 2794, 1593, 1467, 1375, 1154, 1031;
$^1$H-NMR (ppm): 1.04-1.08 (3H, t, J=7.48 Hz), 1.75-1.78 (2H, m), 2.0-2.04 (2H, m), 2.53-2.58 (2H, q, J=7.43 Hz), 3.11-3.16 (4H, m), 4.86 (1H, m), 7.27-7.32 (2H, m), 7.38-7.40 (1H, d, J=7.82 Hz), 7.53-7.55 (2H, d, J=8.82 Hz), 8.06-8.10 (1H, dd, J=8.96, 4.32 Hz), 8.29 (1H, s), 8.59 (1H, bs), 8.72 (1H, bs);
Mass (m/z): 481.1, 483.1 (M+H)$^+$.

Example 66

Preparation of 5-Fluoro-1-[4'-ethyl-3'-(piperidin-4-yl oxy)benzenesulfonyl]-1H-indole hydrochloride Using a similar procedure as given in the Example 7, with some non-critical variations the above derivative was prepared.
Melting Range: 201.46-204.21° C.
IR (cm$^{-1}$): 2966, 2935, 1593, 1461, 1370, 1139, 1037;
$^1$H-NMR (ppm): 1.12-1.15 (3H, t, J=7.43 Hz), 1.92 (2H, m), 2.07-2.12 (2H, m), 2.61-2.66 (2H, q, J=7.23 Hz), 3.12-3.21 (4H, m), 4.76 (1H, m), 6.70-6.71 (1H, d, J=3.45 Hz), 7.06-7.11 (1H, dt, J=9.0 Hz), 7.24-7.26 (1H, dd, J=8.79 Hz), 7.31-7.35 (2H, m), 7.46-7.48 (1H, d, J=3.5 Hz), 8.06-8.10 (1H, q, J=8.96, 4.32 Hz), 8.29 (1H, s), 8.59 (1H, bs), 7.99-8.03 (1H, dd, J=8.95, 4.35 Hz);
Mass (m/z): 403.2 (M+H)$^+$.

Example 67

Preparation of 3-Bromo-5-fluoro-1-[4'-ethyl-3'-(1-methyl piperidin-4-yl oxy)benzenesulfonyl]-1H-indole Using a similar procedure as given in the Example 7, with some non-critical variations the above derivative was prepared.
Melting Range: 133.2-134.5° C.
IR (cm$^{-1}$): 3145, 2969, 2799, 1614, 1589, 1365, 1153;
$^1$H-NMR (ppm): 1.12-1.26 (3H, t, J=7.52 Hz), 1.74-1.79 (2H, m), 1.88-1.94 (2H, m), 2.31 (3H, s), 2.32-2.35 (2H, m), 2.57-2.63 (4H, m), 4.33 (1H, m), 7.08-7.10 (1H, dt, J=8.98, 2.55 Hz), 7.15-7.16 (1H, d, J=2.65 Hz), 7.17 (1H, d, J=2.5 Hz), 7.20-7.22 (1H, d, J=7.97 Hz), 7.35-7.38 (1H, dd, J=7.93, 1.8 Hz), 7.63 (1H, s); 7.95-7.98 (1H, dd, J=9.05, 4.21 Hz);
Mass (m/z): 495.2 (M+H)$^+$.

Example 68

Preparation of 6-Bromo-1-[4'-ethyl-3'-(1-methyl piperidin-4-yl oxy)benzenesulfonyl]-1H-indole Using a similar procedure as given in the Example 7, with some non-critical variations the above derivative was prepared.

IR (cm$^{-1}$): 3144, 2968, 2932, 1589, 1368, 1147;

$^1$H-NMR (ppm): 1.11-1.15 (3H, t, J=7.52 Hz), 1.24-1.27 (2H, m), 1.78 (2H, m), 1.95 (2H, m), 2.25 (3H, s), 2.31 (2H, m), 2.56-2.58 (2H, q, J=7.32 Hz), 4.35 (1H, m), 6.60-6.61 (1H, d, J=3.49 Hz), 7.19-7.21 (1H, m), 7.32-7.39 (4H, m), 7.50-7.53 (1H, d, J=3.67 Hz), 8.19 (1H, s);

Mass (m/z): 477.20 (M+H)$^+$.

Example 69

Preparation of 1-[4'-Ethyl-3'-(1-methyl piperidin-4-yloxy)benzenesulfonyl]-1H-indole Using a similar procedure as given in the Example 7, with some non-critical variations the above derivative was prepared.

IR (cm$^{-1}$): 2934, 2796, 1593, 1491, 1373, 1170, 1041;

$^1$H-NMR (ppm): 1.09-1.13 (3H, t, J=7.52 Hz), 1.74-1.75 (2H, m), 1.89 (2H, m), 2.30 (3H, s), 2.34-2.39 (4H, m), 2.54-2.60 (2H, q, J=7.48); 4.30 (1H, m), 6.64-6.65 (1H, d, J=3.72 Hz), 7.15-7.20 (2H, m), 7.22-7.24 (1H, dt, J=7.97 Hz) 7.28-7.32 (1H, dt, J=8.35, 1.19 Hz), 7.35-7.38 (1H, d, J=7.9, 1.8 Hz), 7.51-7.53 (2H, m), 7.99-8.02 (1H, d, J=8.32 Hz);

Mass (m/z): 399.3 (M+H)$^+$.

Example 70

Preparation of 6-Chloro-1-[4'-ethyl-3'-(1-methyl piperidin-4-yl oxy)benzenesulfonyl]-1H-indole Using a similar procedure as given in the Example 7, with some non-critical variations the above derivative was prepared.

IR (cm$^{-1}$): 2930, 2796, 1594, 1490, 1376, 1169, 1042;

$^1$H-NMR (ppm): 1.11-1.15 (3H, t, J=7.51 Hz), 1.76-1.79 (2H, m), 1.95 (2H, m), 2.31 (3H, s), 2.35-2.39 (2H, m), 2.57-2.62 (4H, m), 4.35 (1H, m), 6.61-6.62 (1H, d, J=3.59 Hz), 7.19-7.21 (2H, m), 7.23-7.24 (1H, d, J=1.48 Hz), 7.34-7.36 (1H, dd, J=7.9, 1.66), 7.42-7.44 (1H, d, J=8.38 Hz), 7.52 (1H, d, J=3.6 Hz), 8.04 (1H, s);

Mass (m/z): 433.3 (M+H)$^+$.

Example 71

Preparation of 5-Fluoro-1-[4'-ethyl-3'-(1-methyl piperidin-4-yl oxy)benzenesulfonyl]-1H-indole Using a similar procedure as given in the Example 7, with some non-critical variations the above derivative was prepared.

IR (cm$^{-1}$): 2930, 2800, 1608, 1495, 1369, 1170, 1044;

$^1$H-NMR (ppm): 1.11-1.14 (3H, t, J=7.52 Hz), 1.76-1.77 (2H, m), 1.88-1.90 (2H, m), 2.31 (3H, s), 2.35-2.37 (2H, m), 2.56-2.61 (4H, m), 4.30 (1H, m), 6.61-6.62 (1H, d, J=3.58 Hz), 6.99-7.06 (1H, dt, J=9.04, 2.47 Hz), 7.15-7.19 (3H, m), 7.34-7.36 (1H, dd, J=7.9, 1.58), 7.56-7.57 (1H, d, J=3.6 Hz), 7.93-7.96 (1H, dd, J=9.02, 4.39 Hz);

Mass (m/z): 417.57 (M+H)$^+$.

Example 72

Preparation of 5-Fluoro-3-methyl-1-[4'-isopropyl-3'-(1-methylpiperidin-4-yl oxy)benzenesulfonyl]-1H-indole Using a similar procedure as given in the Example 7, with some non-critical variations the above derivative was prepared.

IR (cm$^{-1}$): 2941, 1595, 1467, 1369, 1139;

$^1$H-NMR (ppm): 1.13-1.14 (6H, d, J=6.88 Hz), 1.74 (2H, m), 1.88-1.90 (2H, m), 2.20 (3H, s), 2.31 (5H, bs), 2.59 (2H, m), 3.23-3.28 (1H, m), 4.29 (1H, m), 7.00-7.05 (1H, dt, J=2.4, 8.96 Hz), 7.08-7.11 (1H, dd, J=8.67, 2.4 Hz), 7.14 (1H, s), 7.19-7.21 (1H, d, J=8.09 Hz), 7.31-7.35 (2H, m), 7.92-7.96 (1H, dd, J=8.95, 4.35 Hz);

Mass (m/z): 445.5 (M+H)$^+$.

Example 73

Preparation of 5-Bromo-1-[4'-isopropyl-3'-(1-methyl piperidin-4-yl oxy)benzenesulfonyl]-1H-indole Using a similar procedure as given in the Example 7, with some non-critical variations the above derivative was prepared.

IR (cm$^{-1}$): 2956, 1581, 1444, 1373, 1170;

Mass (m/z): 491.2 (MA-H)$^+$;

Example 74

Preparation of 5-Bromo-1-[4'-Chloro-3'-(1-methyl piperidin-4-yl oxy)benzenesulfonyl]-1H-indole Using a similar procedure as given in the Example 7, with some non-critical variations the above derivative was prepared.

IR (cm$^{-1}$): 2939, 1582, 1474, 1377, 1173;

$^1$H-NMR (ppm): 1.82-1.88 (2H, m), 2.0-2.02 (2H, m), 2.32 (3H, s), 2.61 (2H, m), 2.84 (2H, s), 4.34 (1H, m), 6.61-6.62 (1H, d, J=3.69 Hz), 7.26 (1H, s); 7.33-7.35 (1H, dd, J=2.08, 8.34 Hz), 7.40-7.43 (2H, m), 7.49-7.50 (1H, d, J=3.67 Hz), 7.67-7.68 (1H, d, J=1.85 Hz), 7.85-7.87 (1H, d, J=8.8 Hz);

Mass (m/z): 483.1 (M+H)$^+$.

Example 75

Preparation of 6-Methoxy-1-[4'-chloro-3'-(1-methyl piperidin-4-yl oxy)benzenesulfonyl]-1H-indole Using a similar procedure as given in the Example 7, with some non-critical variations the above derivative was prepared.

IR (cm$^{-1}$): 2940, 1582, 1468, 1374, 1173;

$^1$H-NMR (ppm): 1.67-1.81 (2H, m), 1.86-1.91 (2H, m), 2.29 (5H, bs), 2.59-2.61 (2H, m), 3.86 (3H, s), 4.32 (1H, m), 6.58-6.59 (1H, d, J=3.61 Hz), 6.85-6.88 (1H, dd, J=8.6, 2.21 Hz), 7.27 (1H, d, J=1.82 Hz), 7.30-7.4 (4H, m), 7.51-7.52 (1H, d, J=1.97 Hz);

Mass (m/z): 435.3 (M+H)$^+$.

Example 76

Preparation of 5-Bromo-1-[4'-ethyl-3'-(1-methyl piperidin-4-yl oxy)benzenesulfonyl]-1H-indole Using a similar procedure as given in the Example 7, with some non-critical variations the above derivative was prepared.

$^1$H-NMR (ppm): 1.11-1.14 (3H, t, J=7.48 Hz), 1.76-1.77 (2H, m), 1.88-1.90 (2H, m), 2.32 (4H, m), 2.56-2.61 (5H, m), 4.29-4.32 (1H, m), 6.58-6.60 (1H, d, J=3.6 Hz), 7.14 (1H, d, J=1.8 Hz), 7.18-7.19 (1H, d, J=7.96 Hz), 7.34-7.36 (1H, dd, J=7.84 Hz), 7.39-7.41 (1H, dd, J=8.8 Hz), 7.53-7.54 (1H, d, J=3.68 Hz), 7.66-7.67 (1H, d, J=1.84 Hz), 7.88-7.90 (1H, d, J=8.8 Hz).

Mass (m/z): 477.2 (M+H)$^+$;

Example 77

Preparation of 6-Chloro-1-[3'-(1-methyl piperidin-4-yl oxy)benzenesulfonyl]-1H-indole Using a similar procedure as given in the Example 7, with some non-critical variations the above derivative was prepared.

Mass (m/z): 405.3 (M+H)$^+$;

Example 78

Preparation of 6-Chloro-1-[4'-chloro-3'-(piperidin-4-yl oxy)benzenesulfonyl]-1H-indole hydrochloride Using a similar procedure as given in the Example 7, with some non-critical variations the above derivative was prepared.

Melting Range: 258.3-259.5° C.

IR (cm$^{-1}$): 3082, 2935, 2757, 1580, 1390, 1178;

$^1$H-NMR (ppm): 1.76-1.81 (2H, m), 2.0-2.04 (2H, m), 3.10-3.16 (4H, m), 5.01-5.02 (1H, m), 7.30-7.33 (1H, dd, J=8.42, 1.84 Hz), 7.56-7.59 (1H, dd, J=8.41, 2.02 Hz), 7.62-7.64 (1H, d, J=8.42 Hz), 7.69-7.71 (1H, d, J=8.4 Hz), 7.85 (1H, d, J=2.04 Hz), 7.90-7.91 (1H, d, J=3.68 Hz), 8.02-8.03 (1H, d, J=1.48 Hz), 8.71 (2H, bs).

Mass (m/z): 425.2 (M+H)$^+$;

Example 79

Preparation of 4-Chloro-1-[4'-Methyl-3'-(N,N-dimethylamino propoxy)benzenesulfonyl]-1H-indole Using a similar procedure as given in the Example 16, with some non-critical variations the above derivative was prepared.

IR (cm$^{-1}$): 2927, 1376, 1252, 1167, 756, 682;

$^1$H-NMR (ppm): 2.04 (2H, m), 2.19 (3H, s), 2.36 (6H, s), 2.59-2.63 (2H, t); 3.97-4.0 (2H, t, J=6.12), 6.76-6.78 (1H, d, J=3.64 Hz), 7.15-7.18 (1H, d, J=3.88), 7.21-7.23 (3H, m), 7.35-7.37 (1H, d, J=7.86 Hz), 7.59-7.60 (1H, d, J=3.68 Hz), 7.88 (1H, m);

Mass (m/z): 407.4, 409.2 (M+H)$^+$.

Example 80

Preparation of 5-Methoxy-1-[3'-(N,N-dimethylamino ethoxy)benzenesulfonyl]-1H-indole Using a similar procedure as given in the Example 1, with some non-critical variations the above derivative was prepared.

IR (cm$^{-1}$): 2943, 1468, 1370, 1226, 1148, 1031;

$^1$H-NMR (ppm): 2.34 (6H, s), 2.71-2.74 (2H, t, J=5.52 Hz), 3.81 (3H, s), 4.01-4.04 (2H, t, J=5.52 Hz), 6.58-6.59 (1H, d, J=3.6 Hz), 6.91-7.08 (3H, m), 7.28-7.42 (3H, m), 7.49-7.50 (1H, d, J=3.64 Hz), 7.86-7.88 (1H, d, J=9.08 Hz);

Mass (m/z): 375.3 (M+H)$^+$.

Example 81

Preparation of 1-[3'-(N,N-dimethylamino propoxy)benzenesulfonyl]-1H-indole

Using a similar procedure as given in the Example 4, with some non-critical variations the above derivative was prepared.

IR (cm$^{-1}$): 2945, 1445, 1373, 1262, 1174;

$^1$H-NMR (ppm): 1.88-1.95 (2H, m, J=7.20 Hz), 2.20 (6H, s), 2.39-2.42 (2H, t, J=7.12 Hz), 3.95-3.98 (2H, t, J=7.12 Hz), 6.66 (1H, d, J=3.40 Hz), 7.01-7.04 (1H, m), 7.21-7.43 (5H, m), 7.52-7.54 (1H, d, J=7.76 Hz), 7.55-7.56 (1H, d, J=3.7 Hz), 7.98-8.00 (1H, d, J=8.30 Hz);

Mass (m/z): 359.7 (M+H)$^+$.

Example 82

Preparation of 1-[4'-Isopropyl-3'-(N,N-dimethylamino propoxy)benzenesulfonyl]-1H-indole Using a similar procedure as given in the Example 1, with some non-critical variations the above derivative was prepared.

IR (cm$^{-1}$): 2960, 1371, 1172, 1130, 673;

$^1$H-NMR (ppm): 1.12-1.14 (6H, d, J=6.96), 1.93-2.00 (2H, quin, 7.52 Hz), 2.27 (6H, s), 2.43-2.48 (2H, t, 7.16 Hz), 3.20-3.27 (1H, sept, J=6.92 Hz), 3.97-4.00 (2H, t, 6.16 Hz), 6.65-6.66 (1H, dd, J=3.72, 0.64 Hz), 7.20-7.22 (1H, d, J=8.24 Hz), 7.24-7.26 (2H, m), 7.29-7.34 (1H, m), 7.40-7.42 (1H, d, 8.08, 1.84 Hz), 7.53-7.55 (1H, d, J=7.72 Hz), 7.56, (1H, d, J=3.68 Hz), 8.00-8.02 (1H, dd, J=8.32, 0.72 Hz);

Mass (m/z): 401.3 (M+H)$^+$.

Example 83

Preparation of 5-Chloro-1-[4'-chloro-3'-(1-methyl piperidin-4-yl oxy)benzenesulfonyl]-1H-indole Using a similar procedure as given in the Example 7 with some non-critical variations the above derivative was prepared.

IR (cm$^{-1}$): 2961, 1442, 1378, 1258, 1173;

$^1$H-NMR (ppm): 1.80-1.84 (2H, m), 1.97-2.04 (2H, m), 2.36 (3H, s), 2.45 (2H, m), 2.64-2.67 (2H, m), 4.39 (1H, bs), 6.62-6.63 (1H, d, J=3.63 Hz), 7.26-7.29 (2H, m), 7.34-7.36 (1H, dd, J=8.34, 1.94 Hz), 7.41-7.43 (1H, d, J=8.34 Hz), 7.51 (1H, s), 7.51-7.52 (1H, d, J=3.56 Hz), 7.89-7.92 (1H, d, J=8.82 Hz);

Mass (m/z): 439.2, 441.3, 442.3 (M+H)$^+$.

Example 84

Preparation of 1-[4'-Chloro-3'-(1-methyl piperidin-4-yl oxy)benzenesulfonyl]-5-methoxy-3-methyl-1H-indole Using a similar procedure as given in the Example 7, with some non-critical variations the above derivative was prepared.

IR (cm$^{-1}$): 2949, 2362, 1535, 1353, 1258, 1174;

$^1$H-NMR (ppm): 1.72-1.80 (2H, m), 1.84-1.89 (2H, m), 2.19 (3H, s), 2.30 (5I-1, bs), 2.59-2.61 (2H, m), 3.83 (3H, s), 4.31 (1H, m), 6.86-6.87 (1H, d, J=2.32 Hz), 6.90-6.93 (1H, dd, J=8.96, 2.41 Hz), 7.19 (1H, s), 7.24 (1H, d, J=1.76 Hz), 7.29-7.31 (1H, dd, J=8.32, 1.84 Hz), 7.35-7.37 (1H, d, J=8.32 Hz), 7.86-7.88 (1H, d, J=8.96 Hz);

Mass (m/z): 449.3, 451.3 (M+H)$^+$.

Example 85

Preparation of 1-[4'-Ethyl-3'-(1-methyl piperidin-4-yl oxy)benzenesulfonyl]-5-fluoro-3-methyl 1H-indole Using a similar procedure as given in the Example 7, with some non-critical variations the above derivative was prepared.

IR (cm$^{-1}$): 2964, 2783, 1592, 1362, 1252, 1172;

$^1$H-NMR (ppm): 1.10-1.13 (3H, t, J=7.52 Hz), 1.70-1.76 (2H, m), 1.78 (2H, m), 2.19 (3H, s), 2.31 (5H, bs), 2.54-2.60 (4H, m), 4.30 (1H, m), 6.99-7.04 (1H, dt, J=8.98, 2.46 Hz), 7.07-7.10 (1H, dd, J=8.69, 2.46 Hz), 7.13 (1H, d, J=1.38 Hz), 7.15-7.17 (1H, d, J=7.96 Hz), 7.30 (1H, s), 7.32 (1H, dd, J=1.58 Hz); 7.90-7.94 (1H, dd, J=8.96, 4.36 Hz).

Mass (m/z): 431.3 (M+H)$^+$;

Example 86

Food Intake Measurement

Male Wister rats (120-140 grams) obtained from N. I. N. (National Institute of Nutrition, Hyderabad, India) were used. The chronic effect of the compounds of general formula (I) on food intake in well-fed rats was then determined as follows.

The rats were housed in single home cages for 28 days. During this period, the rats were either dosed orally or ip, with a composition comprising a compound of formula (I) or a corresponding composition (vehicle) without the said compound (control group), once a day. The rat is provided with ad libitum food and water.

On 0, 1$^{st}$, 7$^{th}$, 14$^{th}$, 21$^{st}$ and 28$^{th}$ day the rats were left with the pre-weighed amounts of food. Food intake and weight gain were measured on a routine basis. Also a food ingestion method is disclosed in the literature (Kask et al., European Journal of Pharmacology, 414, 2001, 215-224, and Turnball et. al., Diabetes, vol 51, August, 2002, and some in-house modifications). The respective parts of the descriptions are herein incorporated as a reference and they form part of the disclosure.

Some representative compounds have shown the statistically significant decrease in food intake, when conducted in the above manner at the doses of either 10 mg/Kg, or 30 mg/Kg or both.

Example 87

Tablet Comprising a Compound of Formula (I)

| Ingredient | Amount |
|---|---|
| Compound according to example 1 | 5 mg |
| Lactose | 60 mg |
| Crystalline cellulose | 25 mg |
| K 90 Povidone | 5 mg |
| Pregelatinised starch | 3 mg |
| Colloidal silicon dioxide | 1 mg |
| Magnesium stearate | 1 mg |
| Total weight per tablet | 100 mg |

The ingredients were combined and granulated using a solvent such as methanol. The formulation was then dried and formed into tablets (containing about 20 mg of active compound) with an appropriate tablet machine.

Example 88

Composition for Oral Administration

| Ingredient | % wt./wt. |
|---|---|
| Active ingredient | 20.0% |
| Lactose | 79.5% |
| Magnesium stearate | 0.5% |

The ingredients were mixed and dispensed into capsules containing about 100 mg each; one capsule would approximate a total daily dosage.

Example 89

Liquid Oral Formulation

| Ingredient | Amount |
|---|---|
| Active ingredient | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 g |
| Coloring | 0.5 g |
| Distilled water | q.s. to 100 mL |

The ingredients were mixed to form a suspension for oral administration.

Example 90

Parenteral Formulation

| Ingredient | % wt./wt. |
|---|---|
| Active ingredient | 0.25 g |
| Sodium Chloride | qs to make isotonic |
| Water for injection to | 100 mL |

The active ingredient was dissolved in a portion of the water for injection. A sufficient quantity of sodium chloride was then added with stirring to make the solution isotonic. The solution was made up to weight with the remainder of the

Example 91

Suppository Formulation

| Ingredient | % wt./wt. |
| --- | --- |
| Active ingredient | 1.0% |
| Polyethylene glycol 1000 | 74.5% |
| Polyethylene glycol 4000 | 24.5% |

The ingredients were melted together and mixed on a steam bath and poured into molds containing 2.5 grams total weight.

Example 92

Topical Formulation

| Ingredients | Grams |
| --- | --- |
| Active ingredient | 0.2-2 g |
| Span 60 | 2 g |
| Tween 60 | 2 g |
| Mineral oil | 5 g |
| Petrolatum | 10 g |
| Methyl paraben | 0.15 g |
| Propyl paraben | 0.05 g |
| BHA (butylated hydroxy anisole) | 0.01 g |
| Water | 100 mL |

All of the ingredients, except water, were combined and heated to about 60° C. with stirring. A sufficient quantity of water at about 60° C. was then added with vigorous stirring to emulsify the ingredients and then water added q.s about 100 grams.

Example 93

Object Recognition Task Model

The cognition-enhancing properties of compounds of this invention were estimated using a model of animal cognition: the object recognition task model.

Male Wister rats (230-280 grams) obtained from N. I. N. (National Institute of Nutrition, Hyderabad, India) were used as experimental animals. Four animals were housed in each cage. Animals were kept on 20% food deprivation before one day and given water ad libitum throughout the experiment and maintained on a 12 hours light/dark cycle. Also the rats were habituated to individual arenas for 1 hour in the absence of any objects.

One group of 12 rats received vehicle (1 mL/Kg) orally and another set of animals received compound of the formula (I) either orally or i.p., before one hour of the familiar (T1) and choice trial (T2).

The experiment was carried out in a 50×50×50 cm open field made up of acrylic. In the familiarization phase, (T1), the rats were placed individually in the open field for 3 minutes, in which two identical objects (plastic bottles, 12.5 cm height×5.5 cm diameter) covered in yellow masking tape alone (a1 and a2) were positioned in two adjacent corners, 10 cm. from the walls. After 24 hours of the (T1) trial for long-term memory test, the same rats were placed in the same arena as they were placed in T1 trial. Choice phase (T2) rats were allowed to explore the open field for 3 minutes in presence of one familiar object (a3) and one novel object (b) (Amber color glass bottle, 12 cm high and 5 cm in diameter). Familiar objects presented similar textures, colors and sizes. During the T1 and T2 trial, explorations of each object (defined as sniffing, licking, chewing or having moving vibrissae whilst directing the nose towards the object at a distance of less than 1 cm) were recorded separately by stopwatch. Sitting on an object was not regarded as exploratory activity, however, it was rarely observed.

T1 is the total time spent exploring the familiar objects (a1+a2).

T2 is the total time spent exploring the familiar object and novel object (a3+b).

The object recognition test was performed as described by Ennaceur, A., Delacour, J., 1988, A new one-trial test for neurobiological studies of memory in rats—Behavioral data, Behay. Brain Res., 31, 47-59.

Some representative compounds have shown positive effects indicating the increased novel object recognition viz; increased exploration time with novel object and higher discrimination index.

Example 94

Chewing/Yawning/Stretching Induction by 5-$HT_6$ R Antagonists

Male Wister rats weighing 200-250 grams were used. Rats were given vehicle injections and placed in individual, transparent chambers for 1 hour each day for 2 days before the test day, to habituate them to the observation chambers and testing procedure. On the test day, rats were placed in the observation chambers immediately after, drug administration and observed continuously for yawning, stretching, and chewing behaviors from 60 to 90 minutes after drug or vehicle injections. 60 minutes prior to the drug administration Physostigmine, 0.1 mg/kg i.p, was administered to all the animals. Average number of yawns, stretches and vacuous chewing movements during the 30 minutes observation period were recorded.

Reference: (A) King M. V., Sleight A., J., Woolley M. L., and et. al., Neuropharmacology, 2004, 47, 195-204. (B) Bentey J. C., Bourson A., Boess F. G., Fone K. C. F., Marsden C. A., Petit N., Sleight A. J., British Journal of Pharmacology, 1999, 126 (7), 1537-1542).

Example 95

Water Maze

The water maze apparatus consisted of a circular pool (1.8 m diameter, 0.6 m high) constructed in black Perspex (TSE systems, Germany) filled with water (24±2° C.) and positioned underneath a wide-angled video camera to track animal. The 10 $cm^2$ perspex platform, lying 1 cm below the water surface, was placed in the centre of one of the four imaginary quadrants, which remained constant for all rats. The black Perspex used in the construction of the maze and platform offered no intramaze cues to guide escape behavior. By contrast, the training room offered several strong extramaze visual cues to aid the formation of the spatial map necessary for escape learning. An automated tracking system, [Videomot 2 (5.51), TSE systems, Germany] was employed. This program analyzes video images acquired via a digital camera and an image acquisition board that determined path length, swim speed and the number of entries and duration of swim time spent in each quadrant of the water maze.

Reference: (A) Yamada N., Hattoria A., Hayashi T., Nishikawa T., Fukuda H. et. Al., Pharmacology, Biochem. And Behaviour, 2004, 78, 787-791. (B) Linder M. D., Hodges D. B., Hogan J. B., Corsa J. A., et. al., The Journal of Pharmacology and Experimental Therapeutics, 2003, 307 (2), 682-691.

Example 96

Passive Avoidance Apparatus

Animals were trained in a single-trial, step through, light-dark passive avoidance paradigm. The training apparatus consisted of a chamber 300 mm in length, 260 mm wide, and 270 mm in height, constructed to established designs. The front and top were transparent, allowing the experimenter to observe the behavior of the animal inside the apparatus. The chamber was divided into two compartments, separated by a central shutter that contained a small opening 50 mm wide and 75 mm high set close to the front of the chamber. The smaller of the compartments measured 9 mm in width and contained a low-power (6V) illumination source. The larger compartment measured 210 mm in width and was not illuminated. The floor of this dark compartment consisted of a grid of 16 horizontal stainless-steel bars that were 5 mm in diameter and spaced 12.5 mm apart. A current generator supplied 0.75 mA to the grid floor, which was scrambled once every 0.5 seconds across the 16 bars. A resistance range of 40-60 micro ohms was calculated for a control group of rats and the apparatus was calibrated accordingly. An electronic circuit detecting the resistance of the animal ensured an accurate current delivery by automatic variation of the voltage with change in resistance.
Experimental Procedure:
This was carried out as described previously. Adult male Wister rats weighing 200-230 grams were used. Animals were brought to the laboratory 1 hour before the experiment. On the day of training, animals were placed facing the rear of the light compartment of the apparatus. The timer was started once the animal has completely turned to face the front of the chamber. Latency to enter the dark chamber was recorded (usually <20 seconds) and having completely entered the dark compartment an inescapable foot shock of 0.75 mA for 3 seconds was administered to the animal. Animals were then returned to their home cages. Between each training session, both compartments of the chamber were cleaned to remove any confounding olfactory cues. Recall of this inhibitory stimulus was evaluated 24 hours, 72 hours and on 7 day post-training by returning the animal into the light chamber and recording their latency to enter the dark chamber, a criterion time of 300 seconds was employed.
Reference: (A) Callahan P. M., Ilch C. P., Rowe N. B., Tehim A., Abst. 776.19.2004, Society for neuroscience, 2004. (B) Fox G. B., Connell A. W. U., Murphy K. J., Regan C. M., Journal of Neurochemistry, 1995, 65, 6, 2796-2799.

Example 97

Binding Assay for Human 5-HT$_6$ Receptor

Compounds can be tested according to the following the procedures.
Materials and Methods:
Receptor source: Human recombinant expressed in HEK293 cells
Radioligand: [$^3$H]LSD (60-80 Ci/mmol)
Final ligand concentration—[1.5 nM]
Non-specific determinant: Methiothepin mesylate—[0.1 µM]

Reference compound: Methiothepin mesylate
Positive control: Methiothepin mesylate
Incubation Conditions:
Reactions were carried out in 50 µM TRIS-HCl (pH 7.4) containing 10 µM MgCl$_2$, 0.5 mM EDTA for N minutes at 37° C. The reaction was terminated by rapid vacuum filtration onto glass fiber filters. Radioactivity trapped onto the filters was determined and compared to control values in order to ascertain any interactions of test compound(s) with the cloned serotonin 5-HT$_6$ binding site.

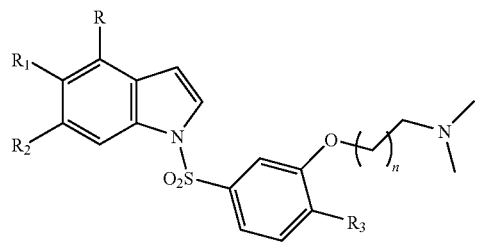

| Example No. | R | $R_1$ | $R_2$ | $R_3$ | n | Radioligand binding data at 5-HT$_6$ R (h) Ki (nM) |
|---|---|---|---|---|---|---|
| 10 | H | H | H | CH$_3$ | 1 | 2.75 |
| 11 | H | F | H | CH$_3$ | 1 | 5.87 |
| 12 | H | Br | H | CH$_3$ | 1 | 28.3 |
| 13 | H | OCH$_3$ | H | CH$_3$ | 1 | 11.20 |
| 15 | H | H | Cl | CH$_3$ | 1 | 1.57 |
| 16 | H | H | H | CH$_3$ | 2 | 1.86 |
| 17 | H | F | H | CH$_3$ | 2 | 12.50 |
| 18 | H | Br | H | CH$_3$ | 2 | 11.80 |
| 19 | H | OCH$_3$ | H | CH$_3$ | 2 | 30.90 |
| 20 | H | OC$_2$H$_3$ | H | CH$_3$ | 2 | 12.40 |
| 21 | H | H | Cl | CH$_3$ | 2 | 13.10 |
| 26 | H | H | H | C$_2$H$_5$ | 1 | 1.90 |
| 30 | H | F | H | C$_2$H$_5$ | 1 | 5.44 |
| 31 | H | H | H | C$_2$H$_5$ | 2 | 35.20 |
| 32 | H | Br | H | C$_2$H$_5$ | 2 | 7.55 |
| 33 | H | H | Cl | C$_2$H$_5$ | 2 | 5.80 |
| 35 | H | F | H | C$_2$H$_5$ | 2 | 18.80 |
| 36 | H | H | H | Pr$^i$ | 1 | 13.90 |
| 43 | H | OCH$_3$ | H | Pr$^i$ | 2 | 62.50 |
| 79 | Cl | H | H | CH$_3$ | 2 | 13.60 |

Percent Inhibition of Specific Binding at 100 nM Concentrations

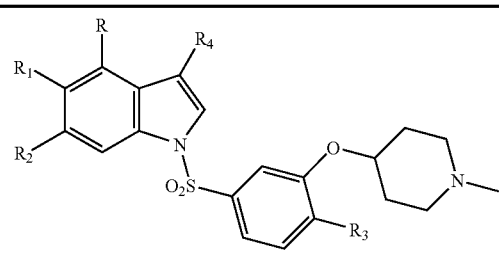

| Example No. | R | $R_1$ | $R_2$ | $R_3$ | $R_4$ | Radioligand binding data at 5-HT$_6$ R (h) % Inhibition of specific binding at 100 nM |
|---|---|---|---|---|---|---|
| 8 | H | F | H | H | H | 61.67 |
| 9 | H | OCH$_3$ | H | H | H | 58.2 |
| 24 | H | F | H | CH$_3$ | H | 89.42 |

-continued

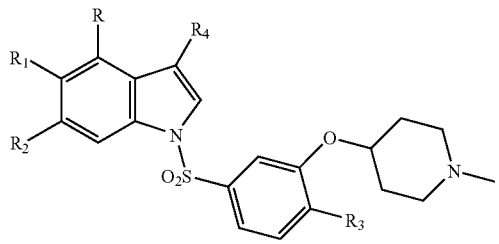

| Example No. | R | $R_1$ | $R_2$ | $R_3$ | $R_4$ | Radioligand binding data at 5-$HT_6$ R (h) % Inhibition of specific binding at 100 nM |
|---|---|---|---|---|---|---|
| 52 | H | $OCH_3$ | H | $Pr^i$ | H | 31.47 |
| 53 | H | F | H | $Pr^i$ | H | 66.86 |
| 54 | H | H | H | $CH_3$ | $CH_3$ | 99.70 |
| 55 | H | $OCH_3$ | H | $C_2H_5$ | H | 88.99 |
| 56 | H | $OCH_3$ | H | $OCH_3$ | H | 88.63 |
| 58 | H | F | H | $OCH_3$ | H | 91.56 |
| 59 | H | F | H | Cl | H | 89.79 |

Literature Reference: Monsma F. J. Jr., et al., Molecular Cloning and Expression of Novel Serotonin Receptor with High Affinity for Tricyclic Psychotropic Drugs. Mol. Pharmacol. (43): 320-327 (1993).

Example 98

5-$HT_6$ Functional Assay Cyclic AMP

The antagonist property of the compounds at the human 5-$HT_6$ receptors was determined by testing their effect on cAMP accumulation in stably transfected HEK293 cells. Binding of an agonist to the human 5-$HT_6$ receptor will lead to an increase in adenyl cyclase activity. A compound that is an agonist will show an increase in cAMP production and a compound that is an antagonist will block the agonist effect.

Human 5-$HT_6$ receptors were cloned and stably expressed in HEK293 cells. These cells were plated in 6 well plates in DMEM/F12 media with 10% fetal calf serum (FCS) and 500 μg/mL G418 and incubated at 37° C. in a $CO_2$ incubator. The cells were allowed to grow to about 70% confluence before initiation of the experiment. On the day of the experiment, the culture media was removed and the cells were washed once with serum free medium (SFM). Two mL of SFM+IBMX media was added and incubated at 37° C. for 10 minutes. The media were removed and fresh SFM+IBMX media containing various compounds and 1 μM serotonin (as antagonist) were added to the appropriate wells and incubated for 30 minutes. Following incubation, the media were removed and the cells were washed once with 1 mL of PBS (phosphate buffered saline). Each well was treated with 1 mL cold 95% ethanol and 5 μM EDTA (2:1) at 4° C. for 1 hour. The cells were then scraped and transferred into Eppendorf tubes. The tubes were centrifuged for 5 minutes at 4° C. and the supernatants were stored at 4° C. until assayed.

cAMP content was determined by EIA (enzyme-immunoassay) using the Amersham Biotrak cAMP EIA kit (Amersham RPN 225). The procedure used is as described for the kit. Briefly, cAMP is determined by the competition between unlabeled cAMP and a fixed quantity of peroxidase-labelled cAMP for the binding sites on anti-cAMP antibody. The antibody is immobilized onto polystyrene microtitre wells precoated with a second antibody. The reaction is started by adding 50 μL, peroxidase-labeled cAMP to the sample (100 μL) pre-incubated with the antiserum (100 mL) for 2 hOurs at 4° C. Following 1 hour incubation at 4° C., the unbound ligand is separated by a simple washing procedure. Then an enzyme substrate, trimethylbenzidine (1), is added and incubated at room temperature for 60 minutes. The reaction is stopped by the addition of 100 mL 1.0 M sulphuric acid and the resultant color read by a microtitre plate spectrophotometer at 450 nm within 30 minutes.

In the functional adenylyl cyclase assay, some of the compound of this invention was found to be a competitive antagonist with good selectivity over a number of other receptors including other serotonin receptors such as 5-$HT_{1A}$ and 5-$HT_7$.

Example 99

Rodent Pharmacokinetic Study

Male wistar rats (230-280 grams) obtained from N. I. N. (National Institute of Nutrition, Hyderabad, India) were used as an experimental animal.

Three to five animals were housed in each cage. Animals were kept on 20% food deprivation before one day and given water ad libitum throughout the experiment and maintained on a 12 hours light/dark cycle. One group of rats received NCE compound (3-30 mg/Kg) orally and another group of animals received same compound through intravenously.

At each time point blood was collected by jugular vein. Plasma was stored frozen at −20° C. until analysis. The concentrations of the NCE compound in plasma were determined using LC-MS/MS method.

Schedule time points: Pre dose 0.25, 0.5, 1, 1.5, 2, 3, 4, 6, 8, 10, 12 and 24 hours after dosing (n=3). The NCE compounds were quantified in plasma by validated LC-MS/MS method using solid phase extraction technique. NCE compounds were quantified in the calibration range of 2-2000 ng/ml in plasma and brain homogenate. Study samples were analyzed using calibration samples in the batch and quality control samples spread across the batch.

Pharmacokinetic parameters Cmax, Tmax, AUCt, AUCinf, half life, volume of distribution, clearance, mean residence time and thereby oral bioavailability were calculated by non-compartmental model using software WinNonlin version 4.1.

Example 100

Rodent Brain Penetration Study

Male Wister rats (230-280 grams) obtained from N. I. N. (National Institute of Nutrition, Hyderabad, India) were, used as an experimental animal Three to five animals were housed in each cage. Animals were kept on 20% food deprivation before one day and given water ad libitum throughout the experiment, and maintained on a 12 hours light/dark cycle. Each group of animals received NCE compound (3-30 mg/Kg) orally or ip.

At each time point blood was collected by jugular vein. Animals will be sacrificed to collect the brain tissue and was homogenized. Plasma and Brain was stored frozen at −20° C. until analysis. The concentrations of the NCE compound in plasma and Brain were determined using LC-MS/MS method.

Schedule time points: Pre dose 0.25, 0.5, 1, 1.5, 2, 3, 4, 6, 8, 10, 12 and 24 hours after dosing (n=3). The NCE compounds were quantified in plasma and brain homogenate by validated LC-MS/MS method using solid phase extraction technique. NCE compounds were quantified in the calibration range of 2-2000 ng/ml in plasma and brain homogenate. Study samples were analyzed using calibration samples in the batch and quality control samples spread across the batch.

Pharmacokinetic parameters Cmax, Tmax, AUCt, AUCinf, half life, volume of distribution, clearance, mean residence time and thereby Cb/Cp, ratio of NCE in brain versus plasma were calculated by non-compartmental model using software WinNonlin version 4.1.

Example 101

Rodent Brain Micro Dialysis Study for Possible Modulation of Neurotransmitters

Male Wister rats (230-280 grams) obtained from N. I. N. (National Institute of Nutrition, Hyderabad, India) were used as an experimental animal.

Group allocation Group 1: Vehicle (Water; 5 mg/kg; p.o.), Group 2: NCE (3 mg/kg; p.o.), Group 3: NCE (10 mg/kg; p.o.)

Surgical Procedure: Rats were anesthetized with chloral hydrate and placed in Stereotaxic frame. Guide cannula (CMA/12) was placed at AP: −5.2 mm, ML: +5.0 mm relative from bregma and DV: −3.8 mm from the brain surface according to the atlas of Paxinos and Watson (1986). While the animal was still anesthetized, a micro dialysis probe (CMA/12, 4 mm, PC) was inserted through the guide cannula and secured in place. After surgery recovery period of 48-72 hours was maintained before subjecting the animal for study.

A day prior to study animals were transferred to home cages for acclimatization and implanted probe was perfused overnight with a modified Ringer's solution comprised of: 1.3 µM CaCl2 (Sigma), 1.0 µM MgCl$_2$ (Sigma), 3.0 µM KCl (Sigma), 147.0 µM NaCl (Sigma), 1.0 µM Na$_2$HPO$_4$.7H$_2$O and 0.2 µM NaH$_2$PO$_4$.2H$_2$O and 0.3 µM neostigmine bromide (Sigma) (pH to 7.2) at a rate of 0.2 µL/minute set by a microinfusion pump (PicoPlus, Hayward). On the day of experiment perfusion rate was changed to 1.2 µL/minutes and allowed for 3 hours stabilization. After stabilization period, four basals were collected at 20 minutes intervals before dosing. Dialysate samples were collected in glass vials using CMA/170 refrigerated fraction collector.

Vehicle or NCE (3 mg/kg or 10 mg/kg) was administered by gavage after four fractions had been collected. The perfusate was collected until 6 hours after administration.

Acetylcholine concentrations in dialysate samples were measured by LC-MS/MS (API 4000, MDS SCIEX) method. Acetylcholine is quantified in the calibration range of 0.250 to 8.004 ng/mL in dialysates.

On completion of the microdialysis experiments, the animals were sacrificed and their brains were removed and stored in a 10% formalin solution. Each brain was sliced at 50µ on a cryostat (Leica) stained and examined microscopically to confirm probe placement. Data from animals with incorrect probe placement were discarded.

Microdialysis data were expressed as percent changes (Mean±S.E.M.) of baseline that was defined as the average absolute value (in fM/10 µL) of the four samples before drug administration.

Effects of NCE (3 & 10 mg/kg) and Vehicle treatments were statistically evaluated by one-way ANOVA followed by Dunnett's multiple comparison tests. In all statistical measures, a $p<0.05$ was considered significant. The Graph Pad Prism program statistically evaluated the data.

We claim:
1. A compound of formula (I)

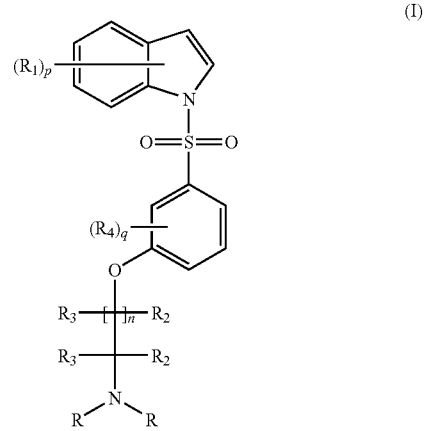

wherein $R_1$ represents hydrogen, fluorine, chlorine, bromine, methyl, methoxy, ethoxy; and R is methyl; and $R_2$ may be same or different and each independently represent hydrogen, methyl or ethyl; and $R_3$ is hydrogen; and $R_4$ may be same or different and each independently represent hydrogen, methyl, ethyl or isopropyl; and "n" represents 0 to 4;

"p" represents 0 to 6; and

"q" represents 0 to 4.

2. A compound, selected from the group consisting of:
1-[3'-(N,N-dimethylamino ethoxy)benzenesulfonyl]-1H-indole;
5-Fluoro-1-[3'-(N,N-dimethylamino ethoxy)benzenesulfonyl]-1H-indole;
5-Bromo-1-(3'-[N,N-dimethylamino ethoxy)benzenesulfonyl]-1H-indole;
5-Fluoro-1-[3'-(N,N-dimethylamino propoxy)benzenesulfonyl]-1H-indole;
5-Bromo-1-[3'-(N,N-dimethylamino propoxy)benzenesulfonyl]-1H-indole;
1-[3'-(N,N-Dimethylamino propoxy)benzenesulfonyl]-5-methoxy-1H-indole;
1-[4'-Methyl-3'-(N,N-dimethylamino ethoxy)benzenesulfonyl]-1H-indole;
5-Fluoro-1-[4'-methyl-3'-(N,N-dimethylamino ethoxy)benzenesulfonyl]-1H-indole,
5-Bromo-1-[4'-methyl-3'-(N,N-dimethylamino ethoxy)benzenesulfonyl]-1H-indole;
1-[4'-Methyl-3'-(N,N-dimethylamino ethoxy)benzenesulfonyl]-5-methoxy-1H-indole;
5-Ethoxy-1-[4'-methyl-3'-(N,N-dimethylamino ethoxy)benzenesulfonyl]-1H-indole;
6-Chloro-1-[4'-methyl-3'-(N,N-dimethylamino ethoxy)benzenesulfonyl]-1H-indole;
1-[4'-Methyl-3'-(N,N-dimethylamino propoxy)benzenesulfonyl]-1H-indole;
5-Fluoro-1-[4'-Methyl-3'-(N,N-dimethylamino propoxy)benzenesulfonyl]-1H-indole;
5-Bromo-1-[4'-Methyl-3'-(N,N-dimethylamino propoxy)benzenesulfonyl]-1H-indole;
1-[4'-Methyl-3'-(N,N-dimethylamino propoxy)benzenesulfonyl]-5-methoxy-1H-indole;

5-Ethoxy-1-[4'-methyl-3'-(N,N-dimethylamino propoxy) benzenesulfonyl]-1H-indole;
6-Chloro-1-[4'-methyl-3'-(N,N-dimethylamino propoxy) benzenesulfonyl]-1H-indole;
1-[4'-Ethyl-3'-(N,N-dimethylamino ethoxy)benzenesulfonyl]-1H-indole;
5-Bromo-1-[4'-ethyl-3'-(N,N-dimethylamino ethoxy)benzenesulfonyl]-1H-indole;
1-[4'-Ethyl-3'-(N,N-dimethylamino ethoxy)benzenesulfonyl]-5-methoxy-1H-indole;
6-Chloro-1-[4'-Ethyl-3'-(N,N-dimethylamino ethoxy)benzenesulfonyl]-1H-indole;
1-[4'-Ethyl-3'-(N,N-dimethylamino ethoxy)benzenesulfonyl]-5-fluoro-1H-indole;
1-[4'-Ethyl-3'-(N,N-dimethylamino propoxy)benzenesulfonyl]-1H-indole;
5-Bromo-1-[4'-Ethyl-3'-(N,N-dimethylamino propoxy) benzenesulfonyl]-1H-indole;
1-[4'-Ethyl-3'-(N,N-dimethylamino propoxy)benzenesulfonyl]-6-chloro-1H-indole;
1-[4'-Ethyl-3'-(N,N-dimethylamino propoxy)benzenesulfonyl]-5-methoxy-1H-indole;
1-[4'-Ethyl-3'-(N,N-dimethylamino propoxy)benzenesulfonyl]-5-fluoro-1H-indole;
1-[4'-isopropyl-3'-(N,N-dimethylamino ethoxy)benzenesulfonyl]-1H-indole;
1-[4'-Isopropyl-3'-(N,N-dimethylamino ethoxy)benzenesulfonyl]-5-methoxy-3-methyl-1H-indole;
1-[4'-Isopropyl-3'-(1-dimethylamino-2-Propoxy)benzenesulfonyl]-1H-indole;
1-[4'-Isopropyl-3'-(2-dimethylamino-1-propoxy)benzenesulfonyl]-1H-indole;
1-[4'-Isopropyl-3'-(N,N-dimethylamino ethoxy)benzenesulfonyl]-3-methyl-1H-indole;
1-[4'-Isopropyl-3'-(N,N-dimethylamino propoxy)benzenesulfonyl]-3-methyl-1H-indole;
1-[4'-Isopropyl-3'-(N,N-dimethylamino ethoxy)benzenesulfonyl]-5-methoxy-1H-indole;
1-[4'-Isopropyl-3'-(N,N-dimethylamino propoxy)benzenesulfonyl]-5-Methoxy-1H-indole;
1-[4'-Isopropyl-3'-(2-dimethylamino propoxy)benzenesulfonyl]-5-Methoxy-1H-indole;
1-[4'-Isopropyl-3'-(1-dimethylamino-2-propoxy)benzenesulfonyl]-5-methoxy-1H-indole;
1-[4'-isopropyl-3'-(N,N-dimethylamino ethoxy)benzenesulfonyl]-5-fluoro-1H-indole;
1-[4'-Isopropyl-3'-(N,N-dimethylamino propoxy)benzenesulfonyl]-5-fluoro-1H-indole;
1-[4'-isopropyl-3'-(2-dimethylamino propoxy)benzenesulfonyl]-5-fluoro-1H-indole;
1-[4'-Isopropyl-3'-(1-dimethylamino-2-propoxy)benzenesulfonyl]-5-fluoro-1H-indole;
1-[4'-Isopropyl-3'-(N,N-dimethylamino ethoxy)benzenesulfonyl]-5-fluoro-3-methyl-1H-indole;
1-[4'-isopropyl-3'-(N,N-dimethylamino propoxy)benzenesulfonyl]-5-fluoro-3-methyl-1H-indole;
4-Chloro-1-[4'-Methyl-3'-(N,N-dimethylamino propoxy) benzenesulfonyl]-1H-indole;
5-Methoxy-1-[3'-(N,N-dimethylamino ethoxy)benzenesulfonyl]-1H-indole;
1-[3'-(N,N-dimethylamino propoxy)benzenesulfonyl]-1H-indole;
1-[4'-Isopropyl-3'-(N,N-dimethylamino propoxy)benzenesulfonyl]-1H-indole;
a stereoisomer thereof; and a salt thereof.

3. A process for the preparation of compound of formula (I) as claimed in claim 1,

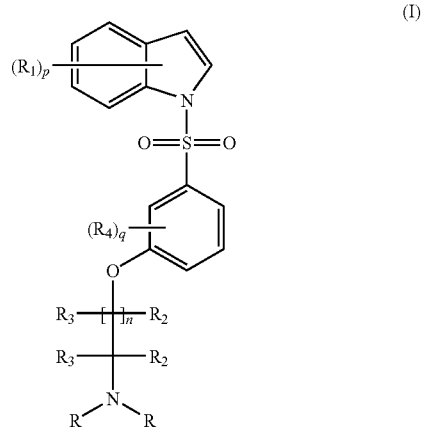

(I)

which comprises, contacting a compound of formula (a)

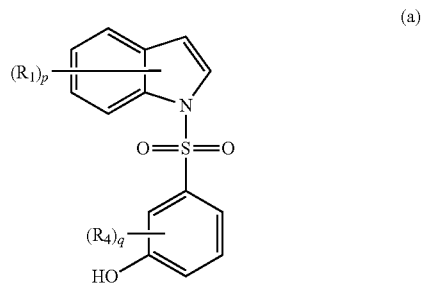

(a)

with amine derivatives

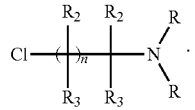

using a suitable base in presence of inert solvent at ambient temperature to obtain a compound of formula (I) wherein all substituents are as defined in claim 1.

4. The process as claimed in claim 3, wherein said base is selected from potassium carbonate, sodium bicarbonate and sodium hydride.

5. The process as claimed in claim 3, wherein said inert solvent is selected from tetrahydrofuran, toluene, ethyl acetate, water, dimethylformamide, dimethyl sulfoxide and dimethyl ether.

6. A pharmaceutical composition comprising a compound as claimed in claim 1:
or its pharmaceutically acceptable salts or any suitable combination thereof, and a pharmaceutically acceptable carrier, diluent or excipient.

7. A method for the pallative treatment of Alzheimer's disease, comprising the step of administering to a patient in need thereof, an effective amount of a compound as claimed in claim 1.

8. A method for the pallative treatment of schizophrenia, comprising the step of administering to a patient in need thereof, an effective amount of a compound as claimed in claim 1.

* * * * *